(12) United States Patent
Fischer et al.

(10) Patent No.: US 9,976,136 B2
(45) Date of Patent: May 22, 2018

(54) RAPID METHODS FOR THE EXTRACTION OF NUCLEIC ACIDS FROM BIOLOGICAL SAMPLES

(71) Applicant: Longhorn Vaccines and Diagnostics, LLC, Bethesda, MD (US)

(72) Inventors: Gerald W. Fischer, Bethesda, MD (US); Luke T. Daum, San Antonio, TX (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 68 days.

(21) Appl. No.: 15/152,871

(22) Filed: May 12, 2016

(65) Prior Publication Data

US 2016/0333339 A1  Nov. 17, 2016

Related U.S. Application Data

(60) Provisional application No. 62/161,527, filed on May 14, 2015, provisional application No. 62/232,666, filed on Sep. 25, 2015.

(51) Int. Cl.
*C12N 15/10* (2006.01)
*C12Q 1/68* (2018.01)

(52) U.S. Cl.
CPC ......... *C12N 15/1013* (2013.01); *C12Q 1/686* (2013.01)

(58) Field of Classification Search
CPC ............................ C12N 15/1013; C12Q 1/686
USPC ......................................................... 536/25.4
See application file for complete search history.

(56) References Cited

U.S. PATENT DOCUMENTS

| | | |
|---|---|---|
| 1,307,416 A | 6/1919 | Pine |
| 2,697,373 A | 12/1954 | Siekmann |
| 4,116,777 A | 9/1978 | Takatsy et al. |
| 4,196,265 A | 4/1980 | Koprowski et al. |
| 4,235,244 A | 11/1980 | Abele et al. |
| 4,315,073 A | 2/1982 | Brown et al. |
| 4,355,102 A | 10/1982 | Quash |
| 4,356,170 A | 10/1982 | Jennings et al. |
| 4,371,091 A | 2/1983 | Gelina |
| 4,372,945 A | 2/1983 | Likhite |
| 4,474,757 A | 10/1984 | Arnon et al. |
| 4,529,702 A | 7/1985 | Bryan |
| 4,554,101 A | 11/1985 | Hopp |
| 4,559,231 A | 12/1985 | Bjerre et al. |
| 4,578,770 A | 3/1986 | Mitani |
| 4,588,680 A | 5/1986 | Bucher et al. |
| 4,596,792 A | 6/1986 | Vyas |
| 4,599,230 A | 7/1986 | Milich et al. |
| 4,601,903 A | 7/1986 | Frasch |
| 4,608,251 A | 8/1986 | Mia |
| 4,634,664 A | 1/1987 | Oestberg |
| 4,634,666 A | 1/1987 | Engleman et al. |
| 4,668,476 A | 5/1987 | Bridgham et al. |
| 4,683,195 A | 7/1987 | Mullis et al. |
| 4,683,202 A | 7/1987 | Mullis |
| 4,707,450 A | 11/1987 | Nason |
| 4,744,982 A | 5/1988 | Hunter et al. |
| 4,746,490 A | 5/1988 | Saneii |
| 4,749,490 A | 6/1988 | Smyth et al. |
| 4,800,159 A | 1/1989 | Mullis et al. |
| 4,803,998 A | 2/1989 | Kezes et al. |
| 4,816,513 A | 3/1989 | Bridgham et al. |
| 4,883,750 A | 11/1989 | Whiteley et al. |
| 4,954,449 A | 9/1990 | Hunter et al. |
| 4,981,782 A | 1/1991 | Judd et al. |
| 4,996,143 A | 2/1991 | Heller et al. |
| 5,091,316 A | 2/1992 | Monthony et al. |
| 5,108,927 A | 4/1992 | Dorn |
| 5,136,019 A | 8/1992 | Judd et al. |
| 5,145,684 A | 9/1992 | Liversidge et al. |
| 5,149,653 A | 9/1992 | Roser |
| 5,163,441 A | 11/1992 | Monthony et al. |
| 5,168,039 A | 12/1992 | Crawford et al. |

(Continued)

FOREIGN PATENT DOCUMENTS

| | | |
|---|---|---|
| EP | 0313224 | 4/1989 |
| EP | 0621339 | 10/1994 |
| EP | 0675199 | 10/1995 |
| EP | 0726316 | 8/1996 |

(Continued)

OTHER PUBLICATIONS

Rohland, et al, "Comparison and Optimization of Ancient DNA Extraction and Supplementary Material," Biotechniques, vol. 42, No. 3, Mar. 1, 2007.

(Continued)

*Primary Examiner* — Jezia Riley

(74) *Attorney, Agent, or Firm* — Remenick PLLC

(57) ABSTRACT

The invention is directed to compositions and methods for rapidly and efficiently extracting nucleic acids and/or targeted nucleic acids sequences from biological samples. The methods of the invention comprise combining the sample with a buffer and magnetic silicon beads and concentrating the beads with a magnet or other electrical field. Liquid may be removed, or not, and an alkaline buffer is added followed by magnetic carboxy beads in a binding buffer so that nucleic acids transfer to the carboxy beads, which can be easily and quickly isolated once again with a magnet. Total nucleic acid extraction is greatly enhanced. Extracted nucleic acids can be analyzed, for example, by PCR wherein the nucleic acids can be identified and characterized. Carboxy beads may also contain a ligand so as to target specific nucleic acid sequences. The invention is also directed to kits comprising the tools and compositions for performing the methods of the invention.

42 Claims, 14 Drawing Sheets

(56) References Cited

U.S. PATENT DOCUMENTS

| | | |
|---|---|---|
| 5,182,109 A | 1/1993 | Tamura et al. |
| 5,186,898 A | 2/1993 | Bridgham et al. |
| 5,187,060 A | 2/1993 | Cerutti et al. |
| 5,234,809 A | 8/1993 | Boom et al. |
| 5,243,030 A | 9/1993 | Judd et al. |
| 5,252,458 A | 10/1993 | Liav et al. |
| 5,290,686 A | 3/1994 | Kendal et al. |
| 5,316,910 A | 5/1994 | Rota et al. |
| 5,399,363 A | 3/1995 | Liversidge et al. |
| 5,482,856 A | 1/1996 | Fell, Jr. et al. |
| 5,503,841 A | 4/1996 | Doyle et al. |
| 5,543,158 A | 8/1996 | Gref et al. |
| 5,545,555 A | 8/1996 | Racioppi et al. |
| 5,552,157 A | 9/1996 | Yagi et al. |
| 5,565,213 A | 10/1996 | Nakamori et al. |
| 5,565,322 A | 10/1996 | Heller |
| 5,567,434 A | 10/1996 | Szoka, Jr. |
| 5,571,511 A | 11/1996 | Fischer |
| 5,589,174 A | 12/1996 | Okuno et al. |
| 5,627,071 A | 5/1997 | Triva |
| 5,631,350 A | 5/1997 | Okuno et al. |
| 5,641,515 A | 6/1997 | Ramtoola |
| 5,656,016 A | 8/1997 | Ogden |
| 5,663,055 A | 9/1997 | Turner et al. |
| 5,679,356 A | 10/1997 | Bonnem et al. |
| 5,691,299 A | 11/1997 | Fabry |
| 5,697,899 A | 12/1997 | Hillman et al. |
| 5,702,944 A | 12/1997 | Racioppi et al. |
| 5,719,020 A | 2/1998 | Liav et al. |
| 5,736,333 A | 4/1998 | Livak et al. |
| 5,738,868 A | 4/1998 | Shinkarenko |
| 5,741,516 A | 4/1998 | Webb et al. |
| 5,766,841 A | 6/1998 | Liav et al. |
| 5,770,219 A | 6/1998 | Chiang et al. |
| 5,779,708 A | 7/1998 | Wu |
| 5,783,208 A | 7/1998 | Venkateshwaran et al. |
| 5,785,975 A | 7/1998 | Parikh |
| 5,795,582 A | 8/1998 | Wright |
| 5,795,587 A | 8/1998 | Gao et al. |
| 5,797,898 A | 8/1998 | Santini, Jr. et al. |
| 5,800,810 A | 9/1998 | Doyle et al. |
| 5,849,489 A | 12/1998 | Heller |
| 5,891,624 A | 4/1999 | Huang |
| 5,945,515 A | 8/1999 | Chomczynski |
| 5,955,074 A | 9/1999 | Fischer |
| 5,958,379 A | 9/1999 | Regenold et al. |
| 6,015,664 A | 1/2000 | Henrickson et al. |
| 6,033,673 A | 3/2000 | Clements |
| 6,060,068 A | 5/2000 | Doyle et al. |
| 6,136,585 A | 10/2000 | Ball et al. |
| 6,162,603 A | 12/2000 | Heller |
| 6,168,915 B1 | 1/2001 | Scholl et al. |
| 6,242,582 B1 | 6/2001 | Reece et al. |
| 6,280,928 B1 | 8/2001 | Scholl et al. |
| 6,306,404 B1 | 10/2001 | LaPosta et al. |
| 6,306,582 B1 | 10/2001 | Scholl et al. |
| 6,312,395 B1 | 11/2001 | Tripp et al. |
| 6,376,172 B1 | 4/2002 | Scholl et al. |
| 6,406,842 B2 | 6/2002 | Scholl et al. |
| 6,440,423 B1 | 8/2002 | Clements et al. |
| 6,451,325 B1 | 9/2002 | Van Nest et al. |
| 6,458,577 B1 | 10/2002 | Huang |
| 6,495,316 B1 | 12/2002 | Scholl et al. |
| 6,500,432 B1 | 12/2002 | Dalemans et al. |
| 6,503,745 B1 | 1/2003 | Chand et al. |
| 6,534,065 B1 | 3/2003 | Makin et al. |
| 6,572,866 B1 | 6/2003 | Torcia |
| 6,573,080 B2 | 6/2003 | Scholl et al. |
| 6,602,510 B1 | 8/2003 | Fikes et al. |
| 6,603,908 B2 | 8/2003 | Dallas et al. |
| 6,603,998 B1 | 8/2003 | King et al. |
| 6,610,293 B1 | 8/2003 | Fischer et al. |
| 6,610,474 B1 | 8/2003 | Huang |
| 6,627,396 B1 | 9/2003 | Swanson et al. |
| 6,632,432 B1 | 10/2003 | Fischer |
| 6,680,308 B1 | 1/2004 | Hassan |
| 6,689,363 B1 | 2/2004 | Sette et al. |
| 6,713,068 B1 | 3/2004 | Audonnet et al. |
| 6,720,409 B2 | 4/2004 | Okuno et al. |
| 6,734,292 B1 | 5/2004 | Omura et al. |
| 6,759,241 B1 | 7/2004 | Hone et al. |
| 6,780,421 B1 | 8/2004 | Haensler et al. |
| 6,793,928 B1 | 9/2004 | van Scharrenburg et al. |
| 6,811,971 B2 | 11/2004 | Klepp et al. |
| 6,855,321 B1 | 2/2005 | Rappuoli et al. |
| 6,875,600 B2 | 4/2005 | Scholl et al. |
| 6,881,835 B2 | 4/2005 | Bai et al. |
| 6,893,814 B2 | 5/2005 | Swanson et al. |
| 6,939,543 B2 | 9/2005 | Fischer et al. |
| 6,946,291 B2 | 9/2005 | Scholl et al. |
| 7,090,853 B2 | 8/2006 | Kapp et al. |
| 7,223,409 B2 | 5/2007 | Nagata et al. |
| 7,279,162 B1 | 10/2007 | Fischer |
| 7,311,671 B2 | 12/2007 | Jung et al. |
| 7,351,413 B2 | 4/2008 | Page et al. |
| 7,357,936 B1 | 4/2008 | Garcon |
| 7,361,352 B2 | 4/2008 | Birkett et al. |
| 7,494,771 B2 | 2/2009 | Picard et al. |
| 7,541,194 B2 | 6/2009 | Mink et al. |
| 7,648,681 B2 | 1/2010 | Meyer et al. |
| 7,718,402 B2 | 5/2010 | Gayral et al. |
| 7,767,804 B2 | 8/2010 | Bair, Jr. et al. |
| 7,794,001 B2 | 9/2010 | Blackwell et al. |
| 8,080,645 B2 | 12/2011 | Fischer et al. |
| 8,084,443 B2 | 12/2011 | Fischer et al. |
| 8,097,419 B2 | 1/2012 | Fischer et al. |
| 8,293,467 B2 | 10/2012 | Fischer et al. |
| 2001/0021501 A1 | 9/2001 | Scholl et al. |
| 2001/0034022 A1 | 10/2001 | Scholl et al. |
| 2001/0036628 A1 | 11/2001 | Scholl et al. |
| 2002/0054882 A1 | 5/2002 | Okuno et al. |
| 2002/0055094 A1 | 5/2002 | Reece et al. |
| 2002/0081567 A1 | 6/2002 | Henrickson et al. |
| 2002/0082395 A1 | 6/2002 | Fischer et al. |
| 2002/0169140 A1 | 11/2002 | Prendergast |
| 2003/0119209 A1 | 6/2003 | Kaylor et al. |
| 2003/0143566 A1 | 7/2003 | Helftenbein |
| 2003/0203357 A1 | 10/2003 | Huang |
| 2003/0215796 A1 | 11/2003 | Scholl et al. |
| 2003/0219442 A1 | 11/2003 | Mikayama et al. |
| 2004/0009126 A1 | 1/2004 | Pilkiewicz et al. |
| 2004/0013673 A1 | 1/2004 | Fischer et al. |
| 2004/0071757 A1 | 4/2004 | Rolf |
| 2004/0082549 A1 | 4/2004 | Jomaa |
| 2004/0086849 A1 | 5/2004 | Shimasaki et al. |
| 2004/0101869 A1 | 5/2004 | Berg et al. |
| 2004/0126789 A1 | 7/2004 | Park et al. |
| 2004/0142319 A1 | 7/2004 | Yu et al. |
| 2004/0170965 A1 | 9/2004 | Scholl et al. |
| 2004/0214272 A1 | 10/2004 | La Rosa et al. |
| 2004/0223976 A1 | 11/2004 | Bianchi et al. |
| 2005/0009008 A1 | 1/2005 | Robinson et al. |
| 2005/0042229 A1 | 2/2005 | Yang et al. |
| 2005/0090009 A1 | 4/2005 | Cormier et al. |
| 2005/0112656 A1 | 5/2005 | Iwaki |
| 2005/0164260 A1 | 7/2005 | Chen |
| 2005/0169941 A1 | 8/2005 | Lees |
| 2005/0170334 A1 | 8/2005 | Mikayama et al. |
| 2005/0181357 A1 | 8/2005 | Peiris et al. |
| 2005/0187213 A1 | 8/2005 | Lang et al. |
| 2005/0227269 A1 | 10/2005 | Lloyd, Jr. et al. |
| 2006/0002939 A1 | 1/2006 | Fischer et al. |
| 2006/0014185 A1 | 1/2006 | Ollikka et al. |
| 2006/0105468 A1 | 5/2006 | Winkler et al. |
| 2006/0121468 A1 | 6/2006 | Allnutt et al. |
| 2006/0134648 A1 | 6/2006 | Chou et al. |
| 2006/0286557 A1 | 12/2006 | Basehore et al. |
| 2007/0078025 A1 | 4/2007 | Pepe |
| 2007/0102946 A1 | 5/2007 | Blackwell et al. |
| 2007/0172835 A1 | 7/2007 | McBride et al. |
| 2007/0196388 A1 | 8/2007 | Dowling et al. |
| 2007/0202497 A1 | 8/2007 | Renuart et al. |
| 2007/0202511 A1 | 8/2007 | Chen et al. |
| 2007/0286871 A1 | 12/2007 | Hickle et al. |

(56) References Cited

U.S. PATENT DOCUMENTS

| | | | |
|---|---|---|---|
| 2008/0032921 | A1 | 2/2008 | Alexander et al. |
| 2008/0050737 | A1 | 2/2008 | Arieli et al. |
| 2008/0069821 | A1 | 3/2008 | Yang et al. |
| 2008/0074521 | A1 | 3/2008 | Olsen |
| 2008/0075708 | A1 | 3/2008 | Yu et al. |
| 2008/0078499 | A1 | 4/2008 | Fenney |
| 2008/0107665 | A1 | 5/2008 | Suckow et al. |
| 2008/0107687 | A1 | 5/2008 | Poulet |
| 2008/0118531 | A1 | 5/2008 | Hoffmann et al. |
| 2008/0139789 | A1 | 6/2008 | Fischer |
| 2008/0145373 | A1 | 6/2008 | Arumugham et al. |
| 2008/0181914 | A1 | 7/2008 | Eichhorn |
| 2008/0260763 | A1 | 10/2008 | Felgner et al. |
| 2009/0048439 | A1 | 2/2009 | Weisburg et al. |
| 2009/0081202 | A1 | 3/2009 | Fischer et al. |
| 2009/0098527 | A1 | 4/2009 | Fischer et al. |
| 2009/0233309 | A1 | 9/2009 | Fischer et al. |
| 2009/0312285 | A1 | 12/2009 | Fischer et al. |
| 2010/0009343 | A1 | 1/2010 | Fischer et al. |
| 2010/0043546 | A1 | 2/2010 | Kandori et al. |
| 2010/0055672 | A1 | 3/2010 | Saghbini |
| 2010/0151477 | A1 | 6/2010 | Cawthon |
| 2010/0221822 | A1 | 9/2010 | Fischer et al. |
| 2010/0311739 | A1 | 12/2010 | Gunaratnam et al. |
| 2011/0159497 | A1 | 6/2011 | Lee et al. |
| 2011/0281754 | A1 | 11/2011 | Fischer et al. |
| 2012/0088231 | A1 | 4/2012 | Fischer et al. |
| 2012/0100529 | A1 | 4/2012 | Fischer et al. |
| 2012/0107799 | A1 | 5/2012 | Daum |
| 2012/0115126 | A1 | 5/2012 | Fischer et al. |
| 2012/0244527 | A1 | 9/2012 | Trinh et al. |
| 2014/0227687 | A1 | 8/2014 | Horlitz et al. |
| 2014/0273100 | A1 | 9/2014 | Saito et al. |

FOREIGN PATENT DOCUMENTS

| | | |
|---|---|---|
| EP | 1081496 | 3/2001 |
| RU | 2150281 | 6/2000 |
| WO | WO 91/02740 | 3/1991 |
| WO | WO1992016619 | 1/1992 |
| WO | WO1992003454 | 5/1992 |
| WO | WO1994009035 | 4/1994 |
| WO | WO1994017106 | 4/1994 |
| WO | WO/14590 | 3/2001 |
| WO | WO2003026567 | 3/2003 |
| WO | WO2003053462 | 7/2003 |
| WO | WO03/095646 | 11/2003 |
| WO | WO2004002451 | 1/2004 |
| WO | WO2004004658 | 1/2004 |
| WO | WO2004043407 | 5/2004 |
| WO | WO2004055205 | 7/2004 |
| WO | WO2004072270 | 8/2004 |
| WO | WO2004084876 | 10/2004 |
| WO | WO2005010186 | 2/2005 |
| WO | WO 2005/042784 | 5/2005 |
| WO | WO2005075642 | 8/2005 |
| WO | WO2005085274 | 9/2005 |
| WO | WO2006041933 | 4/2006 |
| WO | WO2006138444 | 12/2006 |
| WO | WO2007051036 | 5/2007 |
| WO | WO2007056266 | 5/2007 |
| WO | WO2007091030 | 8/2007 |
| WO | WO2007133682 | 11/2007 |
| WO | WO2008079463 | 7/2008 |
| WO | WO2009/085355 | 7/2009 |
| WO | WO2009085355 | 7/2009 |
| WO | WO1997005248 | 9/2009 |
| WO | WO 2010/123908 | 10/2010 |

OTHER PUBLICATIONS

"Development of an Internal Positive Control for Rapid Diagnosis of Avian Influenza, etc.", A.Das, et al., Journal of Clinical Microbiology, Sep. 2006, vol. 44, No. 9, pp. 3065-3073.

De Moreau de Gerbehaye, A.I. et al., "Stable Hepatitis C Virus RNA Detection by RT-PCR During Four Days Storage," BioMed Central, BMC Infectious Diseases, 2:22 (2002).

"Evaluation of PCR Testing of Ethanol-Fixed Nasal Swab Specimens, etc." A. Krafft, et al., Journal of Clinical Microbiology, Apr. 2005, vol. 43, No. 4, pp. 1768-1775.

"Abstracts—27th Annual Meeting for the European Society for Paediatric Infectious Disease, Brussels, Belgium, Jun. 9-13, 2009," The Ped. Infect. Dis. J., 28(6):e1, e75, e229 (Jun. 2009).

"AgPath-ID One-Step RT-PCR Kit," Applied Biosystems, available at http://www.abion.com/techlib/prot/bp_1005.pdf (last visited Aug. 24, 2009).

Lin, B., et al., "Broad-Spectrum Respiratory Tract Pathogen Identification Using Resequencing DNA Microarrays." Genome Res., 16:527-35 (2006).

Buck et al. BioTechniques vol. 27, pp. 528-536, Sep. 1999.

Wolff, C. et al, "Single-Tube Nested PCR With Room-Temperature-Stable Reagents," Cold Spring Harbor Laboratory Press, PCR Methods and Appl., 4:376-79 (1995).

Schultz, C.L., et al., "A Lysis, Storage, and Transportation Buffer for Long-Term, Room-Temperature Preservation of Human Clinical Lymphoid Tissue Samples Yielding High Molecular Weight Genomic DNA Suitable for Molecular Diagnosis," Am. J. Clin. Pathol., 111(6):748-52 (1999).

Characterization of Novel Influenza 2005.

"Collecting, Preserving, Shipping Specimens for the Diagnosis of Avian Influenza (H5N1) Virus Infection: Guide for Field Operations," WHO/CDS/EPR/ARO/2006.1 (2006).

Daum, et al., Abstract—"A Molecular Transport Medium (MTM) for Pathogen Inactivation, Ambient Transport and Preservation of RNA from Clinical Samples," ICAAC, Boston, MA, Sep. 12-15, 2010.

Daum, et al., Abstract and Poster—"Development of a Real Time Reverse-Transcription PCR (RRT-PCR) Assay for Detection of Influenza A H1N1 2009 From Clinical Respiratory Specimens," Pediatric Infectious Disease Conference ESPID, Nice, France, May 5-8, 2009.

Daum, et al., Abstract and Poster—"Development of a Real Time Reverse-Transcription PCR (RRT-PCR) Assay for Detection of Influenza a H1N1 2009 from Clinical Respiratory Specimens," Pediatric Infectious Disease Conference ESPID, Nice, France, May 5-8, 2010.

De Silva at al. Influenza A virus (A/Nonthaburi/102/2009(H1N1)) segment 4 hemagglutinin (HA) gene, partial cds. Genbank Accession No. GQ 132184.1, submitted May 9, 2009.

Spackman, E., et al., "Development of a Real-Time Reverse Transcriptase PCR Assay for Type A Influenza Vrius and the Avian H5 and H7 Hemagglutinin Subtypes," J. Clinic. Mirobiol., 40(9): 3256-60 (2002).

Hindiyeh et al. Journal of Clinical Microbiology, vol. 43, No. 2, pp. 589-595, Feb. 2005.

J. Mahoney et al., "Multiplex RT-PCR for detecting nineteen respiratory viruses," Journal of Clinical Virology, vol. 36, Jan. 1, 2006, p. S9.

"Adamantane Resistance Among Influenza, etc.", JAMA, Feb. 22, 2006, vol. 295, No. 8, pp. 891-894.

Jamie A. Blow et al., "Viral nucleic acid stabilization by RNA extraction reagent," Journal of Virological Methods, 150 (2008), Feb. 4, 2008, pp. 41-44.

"KOD Hot Start DNA Polymerase," Novagen, available at http://www.emdbiosciences.com/ProductDisplay.asp?catno=71086 (last visited Aug. 24, 2009).

Kutyavin et al. 3'-Minor groove binder-DNA probes increase sequence specificity at PCR extension temperatures. Nucleic Acid Res. (2000) vol. 28, No. 2, pp. 655-661.

"Genetic and Antigenic Analysis of the First A/New Calendonia, etc.", L.Daum, et al., Emerging Infectious Diseases, vol. 8, No. 4, Apr. 2002, pp. 408-412.

Canas, L.C., "Clinical Laboratory: Selection, Collection and Transport of Specimens for Viral Cultures." Department of the Air Force, Air Force Institute of Operational Health (AFIOH), Epidemiological Surveillance Division, SDE O1 44-5001, Virol. Proc. Man., 1-8 (2005).

(56) References Cited

OTHER PUBLICATIONS

Daum L.T., et al., "Molecular Analysis of Isolates From Influenza B Outbreaks in the U.S. and Nepal, 2005," Arch. of Virol., 151:1863-1874 (2006).

Daum, L.T. et al., "Real-Time RT-PCR Assays for Type and Subtype Detection of Influenza A and B Viruses," Influenza & Other Resp. Viruses 1(4): 167-75 (2007).

Daum, L.T., et al., "Abstract—Quantification of Influenza A Virus From Nasal and Lung Tissue of Cotton Rats Using Real-Time RT-PCR and Culture," 26th Annual Meeting of the European Society for Pediatric Infectious Diseases, Graz, Austria (2008).

Daum, L.T., et al., "Abstract—Development and Clinical Evaluation of Rapid Real-Time RT-PCR Assays for Detection of Influenza A and B Viruses," 26th Annual Meeting of the European Society for Pediatric Infectious Diseases, Graz, Austria (2008).

Daum, L.T., et al., "Poster—A Novel Specimen Collection Solution for Molecular Diagnostic Applications," The Pediatric Academic Societies (PAS) Annual Meeting, Honolulu, HI (2008).

Daum, L.T., et al., " Poster—A Rapid, Simplified Collection-to-Detection System for Typing and Subtyping Influenza Viruses Using Real-Time RT-PCR and Culture," American Society for Microbiology (ASM) Conference on Emerging Technologies of Medical Importance for the Diagnosis of Infectious Diseases and the Detection of Pathogenic Microbes, Beijing, China (2008).

Daum, L.T., et al., "Poster—Real-Time RT-PCR Detection of Influenza A Virus in Asymptomatic Culture-Negative Cotton Rats," The Pediatric Academic Societies (PAS) Annual Meeting, Honolulu, HI (2008).

Daum, L.T., et al., "A Rapid, Single-Step Multiplex Reverse Transcription-PCR Assay for the Detection of Human H1N1, H3N2 and B Influenza Viruses." J. of Clinic. Virol., 25(3): 345-50 (2002).

Daum, L.T., et al., "Real-Time RT-PCR Detection of Influenza Virus Within Symptomatic and Asymptomatic Family Members," The 48th Annual IDSA/ICAAC, Washington D.C. (2008).

Lowe et al. A computer program for selection of oligonucleotide primers for polymerase chain reactions. Nucleic Acids Research (1990) vol. 18, No. 7, pp. 1757-1761.

Luke T. Daum et al., "Detection and Molecular Characterization of Clinical Influenza A and B Viruses from Original Nasal Wash Specimens Preserved in PrimeStore," (2008).

Luke T. Daum et al., "Portugal Meeting Poster (Introduction, Materials, and Methods, Results, Discussion)," (2008).

"Luminex Confirms Effectiveness of xTAG Respiratory Viral Panel for Swine Flu Surveillance," Medical News Today, available at http://www.medicalnewstoday.com/printerfriendlynews.php?newsid=148498 (May 1, 2009).

"Luminex Receives FDA Clearance for an Update to the xTAG Respiratory Panel Insert Package Insert to Include Data from Two New Publications on 2009 Influenza A/H1N1," available at http://phx.corporate-ir.net/phoenix.zhtml?c=79403&p=irol-newsArticle&Id=1307416&highlight= (Jul. 14, 2009).

Borns, M. et al., "Most Accurate PCR Enzyme Inproved With Hot Start Feature," Biocompare, available at http://www.biocompare.com/technicalarticle/212/Most-Accurate-PCR-Enzyme-Improved-With-Hot-Start-Feature-from-Startagene.html (last visited Aug. 24, 2009).

Denhart, M., and Doraiswamy, V., "Master Your PCR Domain!" Promega Notes, 78: 9-12 (2001).

Master Your PCR Domain.

"Tools of Biochemistry 5A—Ways to Isolate and Purify Proteins and Other Macromolecules", Matthews, et al., Biochemistry, Second Edition, 1996, pp. 152-155.

Tortora, et al., "Tools of Biochemistry 5A—Ways to Isolate and Purify Proteins and Other Macromolecules," Microbiology—An Introduction, pp. 152-55, 4th Ed., The Benjamin/Cummings Publishing Company, Inc., United States (1992).

Matthews, et al., "Immunofluorescence and Fluorescent Antibody Techniques," Biochemistry, pp. 461-63, 2nd Ed., The Benjamin/Cummings Publishing Company, Inc., United States (1996).

Morre, et al., "RNA Amplification by Nucleic Acid Sequence-Based Amplification with an Internal Standard Enables Reliable Detection of *Chlamydia trachomatis* in *Cervical Scrapings and Urine Samples,*" J. of Clinical Microbiol, 34(12): 3108-3114 (1996).

http://www.ncbi.nim.nih.gov/genomes/FLU/SwineFlu2009.html.

NCBI Influenza Virus Resource "CLE I. GenBank Sequence from Pandemic (H1N1) 2009 Viruses". 1237 pages.

Pheng, O.C. Et al., "Temperature Related Storage Evaluation of an RT-PCR Test Kit for the Detection of Dengue Infection in Mosquitoes," (Research Note), Tropical Biomedicine, 22(1):73-6 (2005).

"Single-Step Method of RNA Isolation by Acid Guanidinium, etc.", P. Chomczyniski, et al., Analytical Biochemistry 162, 1987, pp. 156-159.

"PCR Optimization: Reaction Conditions and Components," Applied Biosystems, Part No. 4371091, Revision C, pp. 1-6 available at http://www.appliedbiosystems.com/cms/groups/mcb_marketing/documents/generaldocuments/cms_042520.pdf (last visited Aug. 24, 2009).

"PCR-Ready Clear Supreme," Syntezza Bioscience Ltd., available at http://www.syntezza.com/egt/PCR-Ready_Clear Supreme.pdf (2006).

Ramanujam, R. et al., "Room-Temperature-Stable PCR Reagents," Cold Spring Harbor Laboratory Press, PCR Methods and Appl., 3:75-76 (1993).

Bright, R.A., et al., "Adamantane Resistance Among Influenza A Viruses Isolated Early During the 2005-2006 Influenza Season in the United States," JAMA, 295(8):891-4 (Feb. 22, 2006).

Fouchier, R.A.M. et al., "Characterization of a Novel Influenza A Virus Hemagglutinin Subtype (H16) Obtained From Black-Headed Gulls," J. of Virol. 79(5):2814-22 (Mar. 2005).

"R.A.P.I.D System," Idaho Technology Inc., available at http://www.idahotech.com/Rapid/Rapid-Water.html (last visited Aug. 24, 2009).

Magari, R.T., Assessing shelf life using real-time and accelerated stability tests, BioPharm Nov. 2003.

Rosenstraus, et al., "An Internal Control for Routine Diagnostic PCR: Design, Properties, and Effect on Clinical Performance," J. of Clinical Microbial, 36(1): 191-197 (1998).

Blacksell, S.D. et al., "The Effect of Sample Degradation and RNA Stabilization on Classical Swine Fever Virus RT-PCR and ELISA methods," J. Virol. Methods, 118(1):33-7 (2004).

"Single Tube PCR Kit Manual," Takara Bio Inc., Cat #RR021, V.02.09, pp. 1-6 available at http://www.takara-bio.us/files/manuels/TAK_RR021_TM.pdf (last visited Aug. 24, 2009).

"Taq PCR Master Mix (2x)," USB Corp., (2007).

"TechNotes Newsletter," Applied Biosystems, 14(4):1-37 (2007).

"Immunoflourescence and Fluorescent-Antibody Techniques", Tortora, et al., Microbiology—An Introduction, Fourth Edition, 1992, pp. 461-463.

"USB Taq PCR Master Mix in qPCR," USB Corporation, Tech Tips, 207 (2005).

World Health Organization, "CDC protocol of realtime RTPCR for influenza A (H1N1)," Apr. 28, 2009.

Wiecek, A., "Pocket PCR: The Whole Chain Reaction in His Hand," Biotechniques.com, Oct. 26, 2010.

Wang, Z., et al., "Identifying Influenza Viruses with Resequencing Microarrays," Emerg. Infect. Dis. 12(4):638-46 (2006).

Danila Valmori et al. "Use of human universally antigenic tetanus toxin T cell epitopes as carriers for human vaccination" Journal of Immunology Jul. 15, 1992.

De Folette et al. Vaccine 2006, Jun. 12, vol. 24, No. 44-46, pp. 6597-6601.

Galarza et al. Viral Immunity 2005, vol. 18, No. 2, pp. 365-372.

Arend et al. Infection and Immunity, 2000, vol. 68, No. 6, pp. 3314-3321.

Geysen, et al., "Use of Peptide Synthesis to Probe Viral Antigens for Epitopes to a Resolution of a Single Amino Acid," Proc. Natl. Acad. Sci., 81, pp. 3998-4002 (1984).

Tolman, et al., "Cyclic V3-Loop Related HIV-1 Conjugate Vaccines," Int. J. Peptide Protein Res., 41, pp. 455-466 (1993).

Conley, et al., "Immunogenicity of Synthetic HIV-1 Gp120 V3-Loop Peptide-Conjugate Immunogens," Vaccine, 12(5), pp. 445-451 (1994).

(56) References Cited

OTHER PUBLICATIONS

Schneider, et al., "Induction of CD8+T Cells Using Heterologous Prime-Boost Immunisation Strategies," Immunol. Rev., 170, pp. 29-38 (1999).

Tanghe, et al., "Improved Immunogenicity and Protective Efficacy of a Tuberculosis DNA Vaccine Encoding Ag85 by Protein Boosting," Infect. and Immun., 69(5), pp. 3041-3047 (2001).

Gonzalo, et al., "A Heterologous Prime-Boost Regime Using DNA and Recombinant Vaccinia Virus Expressing the Leishmania infantum P36/LACK Antigen Protects BALB/c Mice from Cutaneous Leishmaniasis," Vaccine, 20, pp. 1226-1231 (2002).

Meyer, et al., "Complement-Mediated Enhancement of Antibody Function for Neutralization of Pseudotype Virus Containing Hepatitis C Virus E2 Chimeric Glycoprotein," J. of Virol., 76(5) pp. 2150-2158 (2002).

Robinson, "New Hope for an AIDS Vaccine," Nat. Rev. Immunol., 2, pp. 239-250 (Apr. 2002).

Lu, et al., "Multiepitope Trojan Antigen Peptide Vaccines for the Induction of Antitumor CTL and Th Immune Responses," J. of Immunol., 172, pp. 4575-4582 (2004).

Westerfield, et al., "Peptides Delivered by Immunostimulating Reconsituted Influenza Virosomes," J. of Peptide Sci., 11(11), pp. 707-712 (2005).

Gerhard, et al., "Prospects for Universal Influenza Virus," Emerging Infectious Diseases, 12(4), pp. 569-574 (Apr. 2006).

Luo, "Structural Biology: Antiviral Drugs Fit for a Purpose," Nature, 443, pp. 37-38 (Sep. 1, 2006).

PepTcell Ltd., "Technology," http://www.peptcell.com/technology.aspx (2007).

Stoloff, et al., "Synthetic Multi-Epitope Peptides Idenitifed in Silico Induce Protective Immunity Against Multiple Influeza Serotypes," Eur. J. of Immunol., 37(9), pp. 2441-2449 (Aug. 2, 2007).

Depla, et al., "Rational Design of a Multiepitope Vaccine Encoding T-Lymphocyte Epitopes for Treatment of Chronic Hepatitis B Virus Infections," J. of Virol., 82(1), pp. 435-450 (Jan. 2008).

Chien et al. J. Clin. Microbiol. 1999, vol. 37, No. 5, 1393-1397.

Ishioka et al. J. Immunol. vol. 162, pp. 3915-3925, 1999.

Lederman et al. Molecular Immunology 1991, vol. 28, No. 11, pp. 1171-1181.

"Monolithic Silica Extraction Tips for Sample Preparation," CP-Analytica, available at http://cp-analytica (last visited Oct. 25, 2010).

Barnard, et al., "Suitability of new chlamydia transport medium for transport of herpes simplex virus," J. of Clin. Microbiol., 24(5): 692-695 (1986).

Eroglu, et al., "Successful cyropreservation of mouse oocytes by using low concentrations of trehalose and dimethylsylfoxide," Biol. of Rep. 80:70-78 (2009).

Gelmi, et al., "Bacertial survival in different transport media," European Congress of Clinical Microbiology and Infectious Diseases (ECCMID), May 28-31, 2000 (poster).

Higashiyama T., "Novel functions and applications of terhalose," Pure Appl. Chem. 74(7): 1263-1269, 2002

Johnson, F.B., "Transport of viral specimens," Clin. Microbiol. Rev. 3(2): 120-131 (1990).

Sponseller, et al., "Influenza A pandemic (H1N1) 2009 virus infection in domestic cat," Emerg. Infect. Dis. (e-publication) (2010).

Miyazaki, et al., "Development of a monolithic silica extraction top for the analysis of proteins," J. Chromatogr. A., 1043(1): 19-25 (2004) [abstract only].

Henke et al., Nucleic Acids Research 25(19): 3957-3958 (1997).

PCT Search Report for PCT/US2016/032033, dated Aug. 16, 2016.

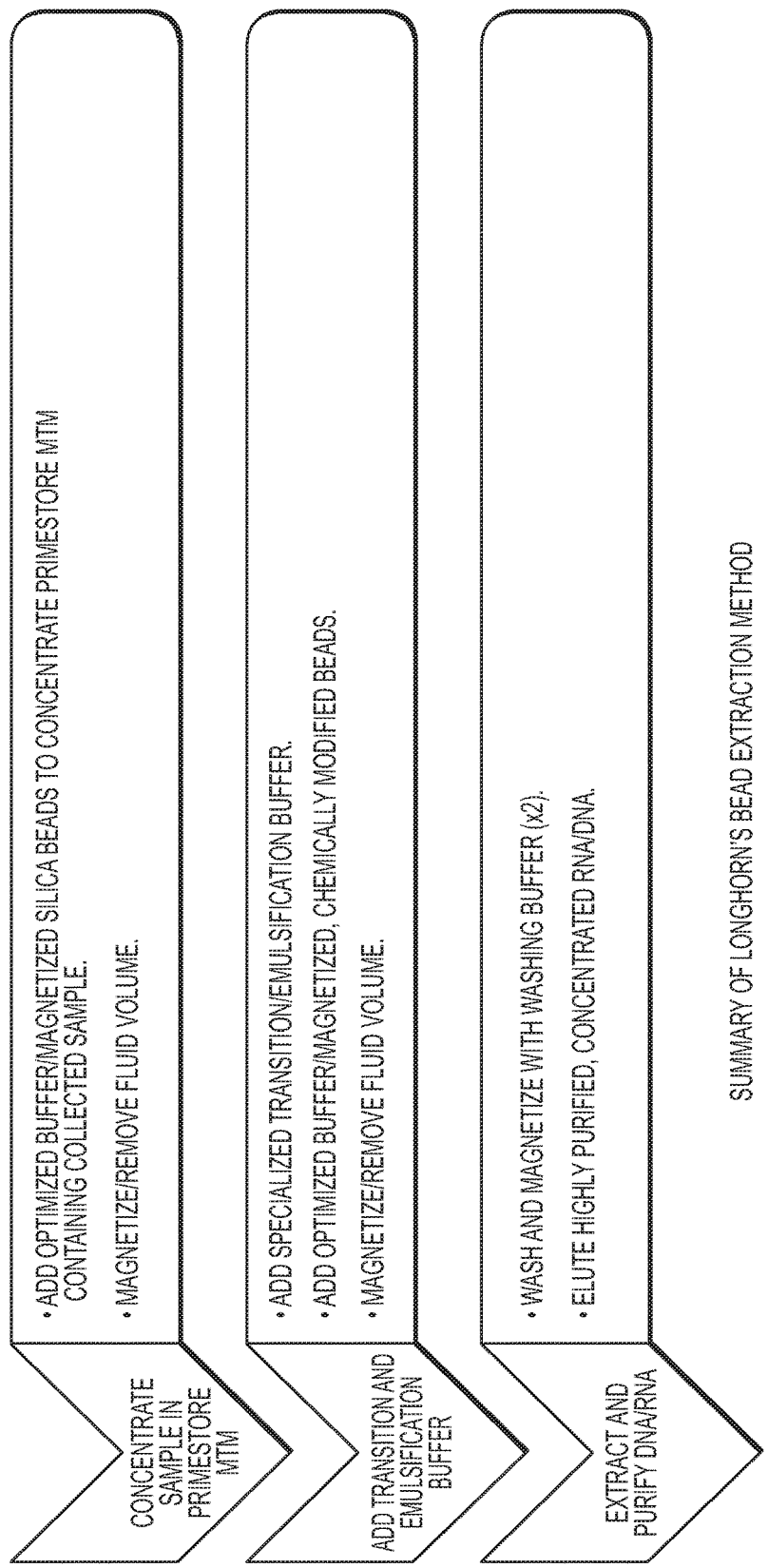

RAPID METHODS FOR THE EXTRACTION OF NUCLEIC ACIDS FROM BIOLOGICAL SAMPLES

REFERENCE TO RELATED APPLICATIONS

This application claims priority to U.S. Provisional Application No. 62/232,666 filed Sep. 25, 2015, and U.S. Provisional Application No. 62/161,527 filed May 14, 2015, the entirety of each of which is specifically incorporated herein.

FIELD OF THE INVENTION

The invention is directed to rapid methods for the extraction of total and/or targeted nucleic acids from a biological sample and, in particular, to tools, methods and compositions containing components that facilitate concentration and isolation/extraction of nucleic acids from samples.

BACKGROUND OF THE INVENTION

The ability to maintain the integrity of nucleic acids in a biological sample (and in particular, those contained in diagnostic samples obtained from human patients), whether the specimen is taken in a remote field location, a doctor's office or in a laboratory, often determines whether the nucleic acids can be successfully analyzed. Typically, nucleic acids in a biological sample will quickly degrade and/or denature at ambient temperatures. This problem is magnified when a specimen is collected at a remote field site, or a significant distance from a doctor's office or laboratory environment, and especially where there may be limited or no access to refrigerator/freezer conditions. Problems associated with the collection and handling of biological specimens are further exacerbated when the desired nucleic acids for downstream analysis include ribonucleic acid (RNA), which is particularly susceptible to degradation by endogenous or exogenous nuclease activity.

Another concern when working with biological specimens is the risk of release of infectious agents to individuals and the environment and, in addition, contamination to the biological specimen itself. This is especially true with regard to the handling of potentially infectious biological agents such as Ebola, avian influenza, severe acute respiratory syndrome (SARS), and many others.

Molecular diagnostics has changed drastically with the advent of polymerase chain reaction (PCR) and thereafter with real-time PCR. Nucleic-acid based detection platforms employing e.g., quantitative real-time PCR (qPCR) or reverse transcriptase PCR (RT-PCR) and quantitative, real-time, reverse transcriptase PCR (qRT-PCR) assays can deliver results in hours versus days required for traditional culture and isolation methods making molecular detection methods the mainstay of modern diagnostic laboratory analysis.

Several commercial companies (e.g., Qiagen [Valencia, Calif., USA], Roche Applied Science [Indianapolis, Ind., USA], Gen-Probe [San Diego, Calif., USA], and bioMérieux [Durham, N.C., USA]) have developed instruments to automate the nucleic acid extraction process from sample isolation to molecular analysis. For example, the Tigris DTS® (Gen-Probe, San Diego, Calif., USA) automates the entire detection process, and in late 2004 was approved by the U.S. Food and Drug Administration (FDA) for simultaneously detecting *Chlamydia trachomatis* and *Neisseria gonorrhoeae* using Gen-Probe's APTIMA COMBO-2® amplified nucleic acid test (NAT) assay.

In view of the requirement for high-quality nucleic acid samples in contemporary detection and assay systems, there is a need in the art for safe and facile collection and analysis of high-quality quality nucleic acids contained within a variety of biological samples and specimens. There is also a need for high efficiency in the collection of nucleic acids. For nucleic acid testing, the issue is not always the absolute amount of the sample collected, but the amount of nucleic acid recovered from the sample. Inefficient recovery of nucleic acids requires repeated collection efforts, which are not always possible. There is also a need for more rapid collection efforts that can be automated for efficient high-throughput methods to recover the highest percentage of nucleic acids possible from the biological sample collected, so that samples can be appropriately and rapidly analyzed for a variety of nucleic acids including RNA and DNA, genes, genomes and specific sequences.

SUMMARY OF THE INVENTION

The present invention encompasses new and useful tools, compositions, and methods of rapidly and efficiently collecting and identifying genes and nucleic acids of interest from a biological sample.

One embodiment of the invention is directed to methods of extracting nucleic acids from a biological sample containing cells and/or microorganisms comprising: adding a matrix material and a buffer to the biological sample, wherein the matrix material binds to the nucleic acids of the sample; isolating matrix material bound to nucleic acids of the sample; adding an intermediate buffer that promotes a release of nucleic acids to form a mixture, adding another magnetic matrix material and a binding buffer to the mixture wherein the magnetic matrix material possess a chemical modification that binds nucleic acids, preferably a specific nucleic acid sequence; exposing the mixture to a magnetic field to concentrate the magnetic matrix material bound to the nucleic acids; adding an extraction buffer to the concentrated magnetic matrix material wherein the nucleic acids are extracted from the magnetic matrix material. Preferably the biological sample comprises human, animal, microbial or plant material and also preferably, the nucleic acids of interest comprise a nucleic acid sequence such as, for example, a cancer marker sequence, cancer marker sequences, sequences indicating the presence of a pathogenic organism or infection, sequences indicating a phenotypic condition of an organism, sequencing indicating a lineage, sequences indicating identifiable characteristics, sequences indicating a mutation, sequences indicating a change from a wild-type or other known sequence, or a combination thereof. Preferred are nucleic acids of interest that are specific to a pathogen such as, for example, a virus, a bacterium, a parasite, a fungus or a combination thereof. In a preferred embodiment, the matrix material comprises magnetic beads of silicone, porcelain, ceramic, plastic, glass or polymer. The matrix material used may or may not disrupt the cells and/or microorganisms of the biological sample. When the cells/microorganisms are disrupted, the matrix materials bind to nucleic acids released from the disrupted cells and/or microorganisms. When the cells/microorganisms are not disrupted, the matrix materials bind to extracellular nucleic acids. Preferably, the buffer lyses cells, inactivates nucleases, sterilizes the sample and maintains the integrity of the nucleic acids. Preferred this buffer contains at least a chaotrope, a detergent, a reducing agent and a chelator at a pH of about 6-8. Alternatively, the buffer may maintain the integrity of cells of the sample and not lyse cells, which is useful for analysis of only excreted nucleic acids and suspended molecules when cells lysis is not desired. Preferably the intermediate buffer causes the release of nucleic acid from the first matrix material and promotes binding to the second matrix material. Also preferably, the intermediate buffer comprises TE, saline, an alkaline solution, NALC (N-acetyl-L-cysteine-sodium citrate-NaOH) or a combination thereof. Preferably the binding buffer contain PEG, a salt such as NaCl, a chelator such as EDTA, a detergent such as Tween-20 and/or Triton X100, a buffering agent such as Tris-HCl, and an alcohol such as ethanol. Preferably, the extraction buffer may comprise a PEG/salt buffer wherein the chemical modification promotes release of the nucleic acids from the magnetic matrix material. Preferably the magnetic field or the another magnetic field is an electro-magnetic field and the extracted nucleic acids are identifiable by molecular analysis such as, for example, PCR which does not involve centrifugation or additional nucleic acid purification. Also preferably, the method is automated for high-throughput analysis of a plurality of biological samples sequences of the extracted nucleic acid can be identified by molecular analysis such as, for example, PCR (polymerase chain reaction). Preferably extraction efficiency, as measured by PCR cycle threshold, is lower as compared with extraction efficiency for a conventional extraction procedure such as, for example, a silica spin column extraction.

Another embodiment of the invention comprises methods of extracting nucleic acids from a biological sample comprising: concentrating nucleic acids of a biological sample; adding an intermediate buffer that is alkaline and magnetic beads in an aqueous or binding buffer comprising PEG to the concentrated nucleic acids to form a mixture, wherein the beads bind to nucleic acids; exposing the mixture to a magnetic field that concentrates the bound magnetic beads and removing the buffer; adding an extraction buffer to the concentrated beads wherein the nucleic acids separate from the magnetic beads; and exposing the mixture to another magnetic field to remove the magnetic beads and isolate the nucleic acids. Preferably concentrating comprises adding magnetic beads and a buffer to the biological sample, wherein the buffer comprises a chaotrope, a detergent, a reducing agent, and a chelator at a pH of about 6-8, removing the magnetic beads, and adding an intermediate buffer suspending the magnetic beads in an. Also preferably analyzing the isolated nucleic acids is by a PCR that does not involve centrifugation or additional nucleic acid purification which is all be automated for high-throughput analysis of a plurality of biological samples. Preferably extraction efficiency, as measured by PCR cycle threshold, is lower as compared with extraction efficiency for a conventional extraction procedure wherein the conventional extraction procedure is a silica spin column extraction.

Another embodiment of the invention comprises kits comprising: a solution that contains a matrix material and a buffer; an intermediate buffer with a pH above 7 and preferably 8 or above or 9 or above; and magnetic carboxy beads in a binding buffer. Preferably the first buffer is a lysis buffer that lyses cell walls, sterilizes the sample, and maintains the integrity of nucleic acids. Alternatively, the buffer may be a non-lysis buffer that maintains the integrity of cell walls where cell lysis would not be desired. Preferred lysis buffer contains a chaotrope, a detergent, a reducing agent and a chelator at a pH of about 6-8. Preferably the matrix material comprises silica dioxide beads, the lysis solution lyses cells, inactivates nucleases and sterilizes a biological sample. Preferably the intermediate buffer comprises a high pH buffer such as pH 8 or above, or pH 9 or above, or pH 10 or above. Preferably the binding buffer is aqueous and comprises one or more of PEG, a salt, a chelator, a detergent and/or an alcohol. Also preferably, kits may further comprise a magnet or electromagnet.

Other embodiments and advantages of the invention are set forth in part in the description, which follows, and in part, may be obvious from this description, or may be learned from the practice of the invention.

DESCRIPTION OF THE FIGURES

FIG. 11. Summary of bead extract method.

FIG. 12 (A-C). qPCR cycle threshold ($C_T$) detection values from RNA/DNA extracted using Qiagen DNA mini vs. Longhorn beads from.

FIG. 13 (A-C). RNA/DNA qPCR efficiency from Qiagen DNA mini vs. Longhorn bead extractions using a 10-fold serial dilution of.

DESCRIPTION OF THE INVENTION

Figure 1:
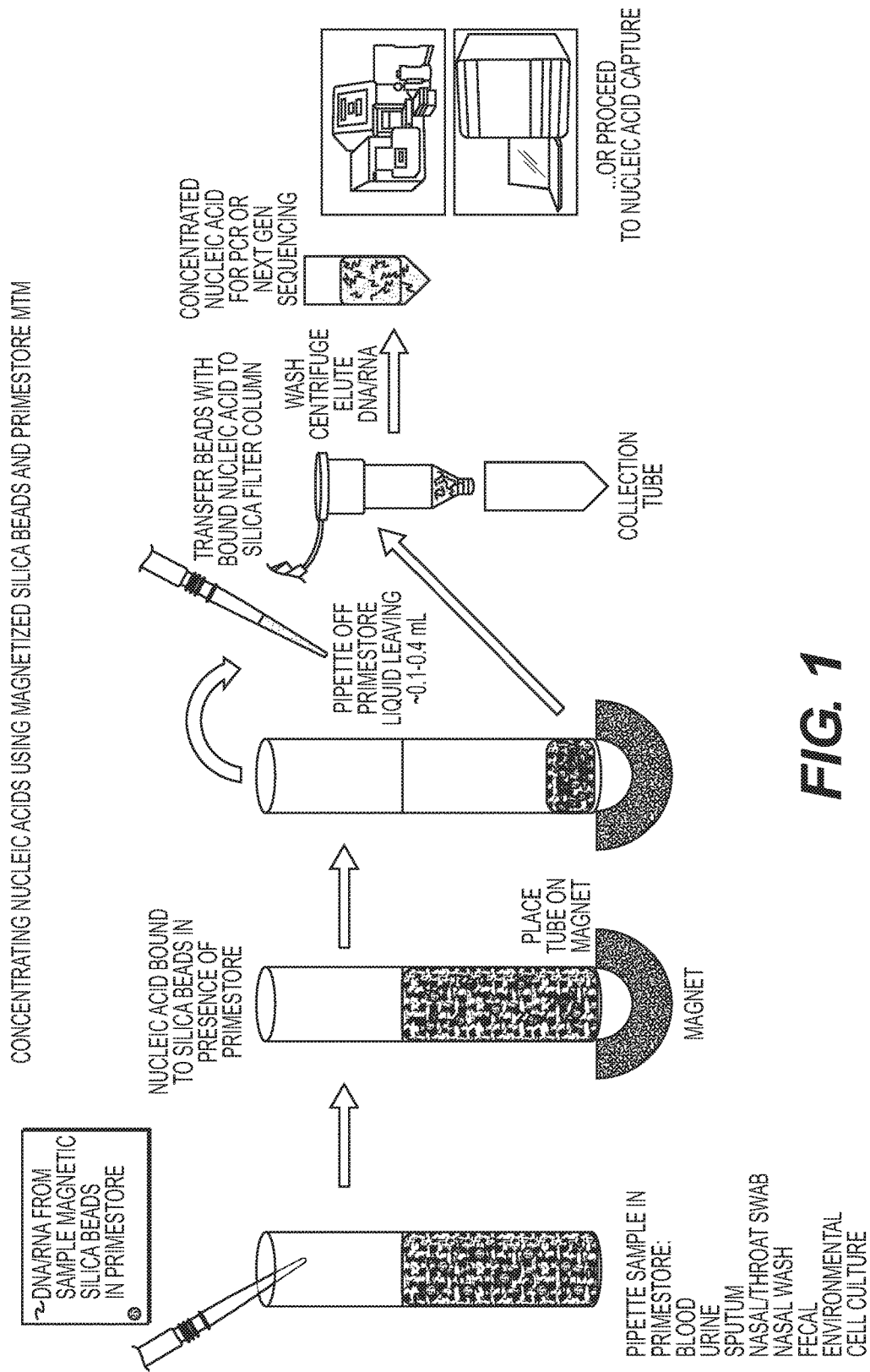
FIG. 1 Concentrating nucleic acids using magnetized silica beds and PrimeStore MTM™.

Extended stabilization, collection, transport, preservation and isolation compositions are in great demand as the ability to screen large populations for diseases and disorders is increasing. Samples or specimens are often located in geographical regions that are remote from a testing facility. As new tools and procedures are developed to increase the speed of nucleic acid recovery, there is a typical loss in the recovery efficiency. High throughput screening results in a loss of the amount and/or quality of nucleic acids recovered from individual samples which compromises subsequent nucleic acid testing.

Molecular diagnosis such as real-time PCR (qPCR) and next-generation sequencing (NGS) continue to improve early detection of infectious disease. Detection is limited by the initial quality and concentration of nucleic acids (RNA/DNA) collected from specimens. PrimeStore MTM (PS-MTM) is a specimen collection and transport medium that kills microbes and preserves nucleic acids at elevated temperatures to maintain high quality RNA/DNA for PCR and NGS. PS-MTM is compatible with most nucleic acid extraction methods including Qiagen silica spin columns and bead-based automated extraction platforms.

It has been surprisingly discovered that desired nucleic acids and preferably nucleic acids can be obtained efficiently and in greater amounts than otherwise available from conventional procedures by collecting the biological sample with affinity chromatography matrix materials according to the compositions and/or methods of the invention. These compositions and methods maximize the amount of nucleic acids extracted from biological sample, while preserving and maintaining both high quality and high fidelity (e.g., sequence fidelity of nucleotides, deoxynucleotides, ribonucleotides, sequences, genes or genomes). Using the procedures of the invention, nucleic acids are rapidly extracted without any need for traditional isolation tools such as spin columns. In addition, the procedures of the invention can be performed in a single vessel and these procedures lend themselves to automation. Also, nucleic acids are spared the deleterious effects routinely observed in conventional samples that are subjected to degradation and contamination during the multiple steps involved with the collection, isolation, storage, and transport processes with a loss overall recovery.

Nucleic acids that can be extracted from biological samples by the compositions and methods of the invention include, but are not limited to all forms of DNA and RNA including but not limited to rRNA, mtDNA, siRNA, ss and ds nucleic acids, extra-cellular DNA and/or RNA, CAN, and artificial nucleotides that may be present. Nucleic acid sequences that can be detected and/or identified include, but are not limited to genes, genomes, cancer marker sequences, sequences indicating the presence of a pathogenic organism or infection, sequences indicating a phenotypic condition of an organism, sequencing indicating a lineage, sequences indicating identifiable characteristics, sequences indicating a mutation, sequences indicating a change from a wild-type or other know sequence, or a combination thereof. In addition, the compositions and methods of the invention are amenable to automation for accurate high-throughput analysis.

One embodiment of the invention is directed to methods of extracting nucleic acids from a biological sample. Preferred methods involved concentrating the nucleic acids from the biological sample by adding to the biological sample a matrix material and a buffer. Preferably the buffer is a lysis buffer that lyses cells, inactivates nucleases, stabilizes one or more of the macromolecules of the sample such as the nucleic acids, and sterilizes the sample, wherein the matrix materials binds to the nucleic acids. Alternatively, the buffer may be a non-lysis buffer that supports cell integrity such that the matrix material binds to extracellular nucleic acids. Bound matrix materials can be isolated and combined with an intermediate buffer forming a mixture that causes the matric material to release the nucleic acids into solution. Additional magnetic beads in an aqueous buffer are added to the mixture, wherein the additional beads possess a chemical modification that binds to the nucleic acids of interest (e.g., a specific sequence or specific structure of interest which may be specific to a pathogenic microorganism or a disorder) that have released from the first matrix material. The mixture is exposed to a magnetic field to concentrate the magnetic beads bound to the nucleic acids of interest. An extraction buffer is added to the concentrated beads wherein the nucleic acids of interest separate from the magnetic beads. Exposing the mixture to another magnetic field allows for separation and/or removal of the magnetic beads from the liquid and isolation of the extracted nucleic acids. Using the methods of the invention, as compared to conventional procedures such as silica spin column extraction, extraction efficiency of nucleic acids of interest is increased at least 5% or more, preferably 10% or more, and more preferably 15% or more, more preferably 20% or more, more preferably 40% or more, more preferably 50% or more, and more preferably 75% or more. This increased efficiency can be the difference between samples being useful and wasted samples. Wasted samples may require repeated collection, although repeated collection is often not possible.

Preferably the extraction of nucleic acids from biological specimens such that living material contained therein is killed or otherwise rendered harmless to pose no or minimal risk of exposure, while at the same time nucleic acids are released for analysis from membranes and other structures that otherwise require additional steps. Compositions to concentrate nucleic acids destroy or render sufficiently inactive enzymes that may be present in the sample that often degrade nucleic acids. Compositions also facilitate the release of DNA/RNA from cells, cell membranes, subcellular structures and/or other structures present in the sample. Preferably, the released nucleic acids bind to a detectable affinity matrix material, also a preferred component of the composition, for ease of isolation and/or analysis of the nucleic acids. Preferably, the composition and the sample are maintained in a single reaction vessel, such that the integrity of the nucleic acids to be detected is at least sufficiently maintained for later diagnostic analysis. Thus, in one-step, the composition of the invention simultaneously: inactivates or kills pathogens that may be present in the sample; inhibits or prevents enzymatic degradation of nucleic acids of the sample that are targeted for later identification, facilitates the release of target nucleic acids from cells and cell structures present in the sample, facilitates separation of released nucleic acids and maintains the integrity of the nucleic acids for later analysis. Preferably, the composition containing the sample does not require refrigeration or freezing and, more preferably, can be maintained at ambient temperatures throughout the sample collection process and at all times prior to analysis. Optionally, the composition may contain predetermined nucleic acid sequences that can serve as one or more internal positive controls (IPC) or one or more internal negative controls (INC) to monitor fidelity, accuracy and/or obtain qualitative and/or quantitative information from the subsequent analysis. Also optionally, compositions may contain carrier nucleic acid such as DNA or RNA.

The ability to achieve all of these desirable functions in a single-step formulation, preferably in a single reaction zone or reaction vessel, is a particularly marked advantage over that presently available. Presently, existing technologies do not include a single-step composition and/or a single vessel system that provides for inactivation of biological components containing nucleic acids, release of the nucleic acids through chemical and/or physical lysis of cells followed by separation or release of RNA/DNA, maintenance of the integrity of the liberated population of nucleic acids, facilitate the isolation of the desired nucleic acids for later analysis, and IPCs and/or INCs to further quantify nucleic acids in the sample. The present invention both stabilizes and preserves the integrity of the nucleic acids from the sample for diagnostic testing, while also providing convenient tools for isolating, concentrating and monitoring, and analyzing total nucleic acids, and/or targeted nucleic acids within the sample. Thus, the compositions and methods of the invention are ideal for clinical, field and deployment use, or for high volume sample collection and extraction procedures. Biological samples collected in compositions of the invention are biologically inactivated, and therefore, may be safely shipped and stored, typically without refrigeration or freezing.

Nucleic acids of the sample that can be detected include, but are not limited to nucleic acids such as DNA and RNA (including for example intracellular or extracellular DNA and/or RNA) or any identifiable sequences therein. Preferably, the nucleic acids to be detected in the collected samples are nucleic acid from a conserved sequence that is indicative of an infection or disorder, or for screening purposes. Nucleic acids of biological samples are typically located within cells, but are also found circulating freely in fluids such as blood and interstitial fluid. These DNA and RNA molecules may be derived from dying cells that break down and release their contents into the blood stream, and are often referred to as circulating nucleic acids (CNA). Detection of specific CNA sequences can be advantageous for determination and identification of a disease or disorder in an individual such as, for example, in acute medicine, diabetes, oncology and fetal medicine to name a few.

The first buffers of the invention preferably contain: a) one or more chaotropes (preferably present in the composition an amount from about 0.5 M to about 6 M); b) one or more detergents (preferably present in the composition an amount from about 0.1% to about 1%); c) one or more chelators (preferably present in the composition in an amount from about 0.01 mM to about 1 mM); d) one or more reducing agents (preferably present in the composition in an amount from about 0.001 M to about 0.3 M); e) one or more defoaming agents (preferably present in the composition in an amount from about 0.0001% to about 0.3%); and (f) one or more matrix materials and preferably affinity chromatography matrix material, and preferably present in the compositions in an effective amount that facilitates extraction and isolation of a diagnostic nucleic acid. Preferred amounts are from about 1 ng to 10 µg per 100 µl.

Exemplary chaotropes include, preferably, guanidine thiocyanate (GuSCN), guanidine hydrochloride (GuHCl), guanidine isothionate, potassium thiocyanate (KSCN), sodium iodide, sodium perchlorate, urea, or any combination thereof. Descriptions of additional exemplary chaotropes and chaotropic salts can be found in U.S. Pat. No. 5,234,809 entitled "Process for Isolating Nucleic Acid," which issued Aug. 10, 1993 (specifically incorporated herein in its entirety by express reference thereto).

Exemplary detergents include, preferably, sodium dodecyl sulfate (SDS), lithium dodecyl sulfate (LDS), sodium taurodeoxycholate (NaTDC), sodium taurocholate (NaTC), sodium glycocholate (NaGC), sodium deoxycholate (NaDC), sodium cholate, sodium alkylbenzene sulfonate (NaABS), N-lauroyl sarcosine (NLS), salts of carboxylic acids (i.e., soaps), salts of sulfonic acids, salts of sulfuric acid, phosphoric and polyphosphoric acid esters, alkylphosphates, monoalkyl phosphate (MAP), and salts of perfluorocarboxylic acids, anionic detergents including those described in U.S. Pat. No. 5,691,299 (specifically incorporated herein in its entirety by express reference thereto), or any combination thereof.

Exemplary reducing agents include, preferably, 2-mercaptoethanol (β-ME), tris(2-carboxyethyl) phosphine (TCEP), dithiothreitol (DTT), formamide, dimethylsulfoxide (DMSO), or any combination thereof. In a preferred embodiment, the reducing agent includes or is TCEP.

Exemplary chelators include, preferably, ethylene glycol tetraacetic acid (EGTA), hydroxyethylethylenediaminetriacetic acid (HEDTA), diethylene triamine pentaacetic acid (DTPA), N,N-bis(carboxymethyl)glycine (NTA), ethylenediaminetetraacetic (EDTA), citrate anhydrous, sodium citrate, calcium citrate, ammonium citrate, ammonium bicitrate, citric acid, diammonium citrate, potassium citrate, magnesium citrate, ferric ammonium citrate, lithium citrate, or any combination thereof. In preferred embodiments, the chelator includes EDTA, a citrate, or a combination thereof. In a more preferred embodiment, the chelator includes EDT.

The compositions of the invention can further include a defoaming agent to prevent the formation of bubbles that typically result from the presence of detergents in the formulation. Defoaming agents facilitate pipetting and handling of the disclosed compositions. Exemplary surfactants/defoaming agents include, preferably, cocoamidopropyl hydroxysultaine, alkylaminopropionic acids, imidazoline carboxylates, betaines, sulfobetaines, sultaines, alkylphenol ethoxylates, alcohol ethoxylates, polyoxyethylenated polyoxypropylene glycols, polyoxyethylenated mercaptans, long-chain carboxylic acid esters, alkonolamides, tertiary acetylenic glycols, polyoxyethylenated silicones, N-alkylpyrrolidones, alkylpolyglycosidases, silicone polymers such as Antifoam A®, or polysorbates such as Tween®, or any combination thereof. In a preferred embodiment, a defoaming agent includes a silicone polymer.

Exemplary nucleic acid capture matrix (NACM) materials include, preferably, agarose, glass, cellulose, polyacrylamide, Sepharose, Sephadex, silica, or another matrix media. Preferably, the NACM material is coated with a nucleic acid binding substance (NABS), such as, for example, nucleic acid (NA) binding proteins, antibodies and chemicals with an affinity for NAs including single-stranded nucleic acid sequences. NACM include materials coupled to specific antibodies or antibody fragments or other nucleic acids or ligands that facilitate extract and/or isolation of the diagnostic molecule of interest. Affinity beads are preferably magnetic beads such as, for example, beads commercially available from Dynabeads®, Life Technologies; TurboBeads, TurboBeads Inc. or PureProteome™, and Millipore. Beads may contain pores of defined sizes that are useful for inclusion or exclusion molecular size chromatography. NACM materials includes matrix media such as, for example, resins that are useful with the compositions and method of the invention such as, preferably, amino acid resins, carbohydrate resins, ion exchange resins, and hydrophobic and hydrophilic resins. The presence of matrix material in the composition of the invention serve to facilitate the release and subsequent capture of nucleic acids from the cells, cell structures, nucleic acids, and biological and non-biological debris of the sample. Preferably, these same matrix materials can then serve to expedite the isolation of the nucleic acids for later analysis through magnetic attraction (e.g., magnetic field, electro-magnetic field, magnet), molecular affinity, ionic or non-ionic interactions, density or specific density, hydrophobic or hydrophilic interactions, shape, color or light emission or absorption or any unique or identifiable distinguishing chemical or physical property.

Buffers of the invention include one or more compounds (each preferably present in the final composition in an amount from about 1 mM to about 1 M). Exemplary buffers include, preferably, tris(hydroxymethyl) aminomethane (Tris), citrate, 2-(N-morpholino)ethanesulfonic acid (MES), N,N-bis(2-hydroxyethyl)-2-aminoethanesulfonic acid (BES), 1,3-bis(tris(hydroxymethyl)methylamino)propane (Bis-Tris), 3-(cyclohexylamino)-1-propanesuhinic acid (CAPS), 3-(cyclohexylamino)-2-hydroxy-1-propanesuhicic acid (CAPSO), 4-(2-hydroxyethyl)-1-piperazineethanesulfonic acid (HEPES), 3-(N-morpholino)propanesulfonic acid (MOPS), 3-(N-morpholino)-2-hydroxypropanesulfonic acid (MOPSO), piperazine-N,N\'-bis(2-hydroxypropanesulfonic acid (POPSO), N-[Tris(hydroxymethyl)methyl]-3-amino propane sulfonic acid (TAPS), N-[Tris(hydroxymethyl)methyl]-3-amino-2-hydroxypropansulfonic acid (TAPSO), N-[Tris(hydroxymethyl)methyl]-2-aminoethanesulfonic acid (TES), N,N-bis(2-hydroxyethyl) glycine (Bicine), N-[tris(hydroxymethyl)methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, or any combination thereof. In a preferred embodiment, the buffer includes a citrate.

The inclusion of one or more of such optional but preferred buffers is desirable to control the pH of the formulations, since it has been found that nucleic acid extraction is optimal in a pH range of about 5 to 8. Preferably, the one or more buffers employed in the disclosed compositions are chosen to provide a significant buffering capacity in the range from a pH of about 5.5 to about 7.5, more preferably within a pH range of about 6 to about 7, and more preferably still, within a pH range of about 6.2 to about 6.8. In exemplary embodiments, the pH of a PrimeStore™ solution (also referred to herein as "PSS") is preferably about 6.9±0.25.

The compositions of the invention may also further optionally include one or more short-chain (preferably from 1- to 6-carbon [i.e., $C_1$-$C_6$] alcohols) alkanols (each preferably present in the composition in an amount from about 1% to about 25%, although higher percentages of the alcohols may be employed if desired). Exemplary short-chain alkanols include linear and branched-chain alcohols, such as, without limitation, methanol, ethanol, propanol, butanol, pentanol, hexanol, or any combination thereof.

The compositions of the invention may also further optionally include one or more additional compounds or reagents including, without limitation, cationic functionalized zwitterionic compounds such as betaines (including, without limitation, N,N,N-trimethylglycine, cocamidopropyl betaine, and the like), albuminoids (including, without limitation, ovalbumin, and the serum albumins of bovine, equine, or human origin), and osmolytes (including, without limitation, trimethylamine N-oxide (TMAO), dimethylsulfoniopropionate, sarcosine, and saccharides or sugar alcohols including, without limitation, trehalose, maltose, rhamnose, sucrose, arabinose, fucose, mannitol, sorbitol, adonitol, and the like).

Preferably, the compositions of the invention provide sufficient buffering capacity to adequately stabilize the populations of polynucleotides obtained from a sample, and will, most preferably, be buffered to a pH of about 6.4 to 6.9 during formulation, and will maintain the isolated populations of polynucleotides in a similar pH range when the sample is contacted with the storage/collection formulations described herein. Buffering capacity of the buffer and/or the composition is preferably maximized by matching the buffer's pKa value with the pH of the composition. Variations between pKa and pH are preferably equal to or less than ±1.0, ±0.75, ±0.5 or ±0.25. Preferably the buffering capacity variation between pKa and pH is +1.0, +0.75, +0.5 or +0.25, or −1.0, −0.75, −0.5 or −0.25, which may relate to the particular buffer used and the initial pH of the composition before buffer is added as determined by one skilled in the art.

The compositions of the present invention will typically at least substantially inactivate, and preferably entirely inactivate, any endogenous or exogenous RNAses, DNAses or proteases present in the sample, such that the nucleic acids of the sample are substantially free of any degradation, and preferably do not degrade, or lose integrity, during the collection, lyses, concentration, storage, and transport of the sample for subsequent in vitro analyses.

Exemplary formulations of the storage/transport/collection compositions of the invention are described in the examples herein, and include, without limitation, a composition that includes about 4 M of a chaotrope (such as guanidine thiocyanate, guanidine hydrochloride, guanidine isocyanate, or any combination thereof), about 10 mM to 30 mM of a chelator (such as EGTA, HEDTA, DTPA, NTA, EDTA, citrate anhydrous, sodium citrate, calcium citrate, ammonium citrate, ammonium bicitrate, citric acid, diammonium citrate, ferric ammonium citrate, lithium citrate, or any combination thereof), about 0.25% of a detergent (such as SDS, LDS, NaTDC, NaTC, NaGC, NaDC, sodium cholate, NaABS, NLS, or any salt or combination thereof), about 0.1 M of a reducing agent (such as β-ME, DTT, DMSO, formamide, TCEP, or any combination thereof), about 0.1% of a surfactant/defoaming agent (such as a silicone polymer [e.g., Antifoam A®] or a polysorbate [e.g., Tween®], or any combination thereof), and about 1.0 μg/100 μl of magnetic affinity beads.

Additional exemplary formulations of the specimen collection compositions of the invention include, without limitation, a composition that includes about 3 M of a chaotrope (such as guanidine thiocyanate, guanidine hydrochloride, guanidine isocyanate, or any combination thereof), about 1 mM of 0.5 M reducing agent (such as, e.g., β-ME, TCEP, formamide, DTT, DMSO, or any combination thereof), about 1 to about 10 mM of a chelator (such as, e.g., EGTA, HEDTA, DTPA, NTA, EDTA, citrate anhydrous, sodium citrate, calcium citrate, ammonium citrate, ammonium bicitrate, citric acid, diammonium citrate, ferric ammonium citrate, lithium citrate, or any combination thereof), about 0.25% of a detergent (such as SDS, LDS, NaTDC, NaTC, NaGC, NaDC, sodium cholate, NaABS, NLS, or any salt or combination thereof), and optionally but preferably about 0.0002% of a defoaming agent (also referred to as an antifoaming agent) (such as a silicone polymer or a polysorbate, or any combination thereof), about 100 mM of a buffer (such as Tris, MES, BES, Bis-Tris, HEPES, MOPS, bicarbonate, citrate, phosphate, or any combination thereof), and about 1.0 μg/100 μl of magnetic affinity beads.

Another exemplary formulation of the disclosed polynucleotide isolation and stabilization compositions include, without limitation, a composition that includes about 1 to about 4 M of a chaotropic agent such as guanidine thiocyanate, guanidine hydrochloride, or guanidine isocyanate; about 0.5 to 100 mM of a chelating agent such as EDTA, or sodium citrate, or both; about 0.1 to about 1% of an anionic detergent such as SDS or N-lauroyl sarcosine, sodium salt; about 0.001% to about 0.0001% of a surfactant or wetting agent such as the silicone polymer, Antifoam A®, e); about 10 to about 500 mM of a buffering agent such as Tris-HCl; about 10% to about 25% of a short-chain alkanol such as ethanol, and about 1.0 μg/100 μl of magnetic affinity beads.

In particular embodiments, the invention provides a composition that includes about 2.5 M guanidine thiocyanate; about 0.5 mM TCEP; about 10 mM sodium citrate; about 0.4% N-lauroyl sarcosine, sodium salt; about 0.0002% Antifoam A, about 100 mM Tris-HCl, about 0.1 mM EDTA; about 23% ethanol, and about 1.0 μg/100 μl of magnetic affinity beads.

The invention also provides a method for obtaining a population of nucleic acids from a sample. The method generally involves associating the sample with an amount of one of the compositions of the invention under conditions effective to obtain a population of nucleic acids from the sample. The invention optionally includes a facilitated release of the DNA/RNA from cells or cell structures of the biological sample and an affinity concentration of the desired population of nucleic acids for later nucleic acid and/or sequence analysis.

The invention also provides a method of preparing a one-step aqueous formulation of the collection/lysis/transport/storage compositions described herein for the collection of nucleic acids such as RNA and/or DNA. In an overall sense, the method generally involves combining one or more chaotropes and nuclease-free water at a temperature of about 20° C. to 90° C. in a reaction zone; then combining the dissolved one or more chaotropes with one or more reducing agents, one or more chelators, and one or more detergents in the reaction zone to form an intermediate composition; optionally combining a silicone polymer with the intermediate composition in an amount sufficient to minimize foaming during further preparation of the one-step aqueous formulation; combining a sufficient amount of buffer to the intermediate composition to maintain a pH of about 6 to 7.0; optionally combining a second chelating agent to the reaction zone; then increasing the temperature of the second intermediate composition to about 60° C. to 95° C. for about 1 to 30 minutes and lowering the temperature to ambient conditions; optionally then combining a $C_{1-6}$ alcohol with the contents of the reaction zone; and optionally adjusting the pH to be about 6.4 to 6.9 and adding the nucleic acid capture material.

In additional embodiments, the invention provides a method for preparing one-step aqueous formulations adapted to obtain a population of nucleic acids from a biological sample or specimen. This method generally involves at least the steps of: a) contacting the sample with an amount of the one-step aqueous formulation effective to: i) at least substantially kill or inactivate potentially-infectious pathogens in the sample; ii) at least chemically or physically lyse a portion of cells to release the desired nucleic acids from the sample; and iii) at least substantially inhibit or prevent the released nucleic acids in the sample from further hydrolysis or enzymatic degradation, modification, or inactivation, so as to obtain the population of the desired nucleic acids from the sample.

Preferably, the methods of the invention will include at least contacting the sample with an amount of one or more of the disclosed compositions at a temperature of from 0° C. to about 40° C. (more preferably at a temperature of 4° C. to about 35° C., and still more preferably at a temperature of 10° C. to about 30° C. or ambient temperatures) for a period of time of at least 15 minutes, more preferably at least 30 minutes, and more preferably at least 8 to 24 hours. During contact with the composition and for all times thereafter, the desired nucleic acids remain substantially intact so as to be detectable without incurring substantial deterioration, degradation, enzymatic cleavage, and/or digestion, modification, or other processing.

Preferably, the integrity of a population of nucleic acids released from the sample into the composition are substantially maintained, even when the composition comprising the sample is stored at ambient temperatures, and even for prolonged periods of time, including, without limitation, storage for greater than about 2 days, greater than about 5 days, greater than about 10 days, greater than about 20 days, or even greater than about 30 days or more. Likewise, it is desirable that the integrity of a population of nucleic acids released from the sample into the composition will be substantially maintained, even when the composition comprising the sample is stored at subtropical and tropical temperatures—even for prolonged periods of time, including, without limitation, storage for greater than or equal to about 5 days, greater than or equal to about 10 days, greater than or equal to about 15 days, or even greater than or equal to about 20, about 25, about 30, about 35, about 40, about 60, or about 90 days or even greater.

In the practice of the present methods, it is preferable that at least one or more biological cells contained within the sample are substantially lysed to release at least a first population or first plurality nucleic acids contained within such cells into the composition. Preferably, the components of the disclosed composition are sufficient to release and thereafter isolate through affinity binding to a matrix material such a population from all or substantially all of the unwanted cellular/tissue and/or sample debris (including, without limitation, lipids, phospholipids, peptides, proteins, polysaccharides, lipopolysaccharides, polyols, cellular organelles, membrane components, and such like).

It is also desirable in the practice of the present methods that when one or more microbes, viruses, fungi, and/or other pathogens or organisms of interest are present in, on, or about the sample when collected, such microbes, viruses, fungi, and/or other pathogens or organisms of interest will be lysed, sufficiently inactivated, or substantially killed upon contact with the composition, which facilitates safe handling of the sample by the practitioner. Preferably, one or more components of the disclosed composition are effective to render a pathogenic sample substantially or preferably entirely, non-pathogenic without the need for adding additional components to the composition. However, in certain applications, it may also be desirable to include one or more additional anti-microbial, anti-viral, or anti-fungal agents to the compositions to render them substantially non-pathogenic, and thus, safe for handling by the practitioner.

Preferably, the composition containing the sample is at least sufficiently stable to permit storage of the sample in the composition at ambient, near-ambient, or even colder or warmer conditions at least substantially (or entirely) from the time of specimen or sample collection substantially until the time of analyzing or characterizing at least a first population of nucleic acids from within the sample. As used herein, "ambient temperature" can refer to temperatures of about 18° C. to 25° C., or in some embodiments, more preferably from about 20° C. to about 22° C.

Preferably, composition containing the sample suspected of containing desired nucleic acids stabilize and isolate the nucleic acids to the extent that they either remain at least substantially non-degraded (i.e., at least substantially stable) even upon prolonged storage of the composition at ambient, refrigerator, or sub-zero temperatures. It is desirable that this stability provides that at least about 70%, at least about 85%, more preferably at least about 90%, more preferably at least about 95%, or even more preferably, at least about 98% of the nucleic acids contained within the stored sample will not be degraded upon prolonged storage of the sample. In certain embodiments, substantially all of the desired nucleic acids contained within the sample will be stabilized such that their original integrity is preserved during the collection, lysis, storage, and transport of the processed sample.

Another embodiment of the invention comprises the surprising synergy of magnetic beads with MTM (e.g. Prime-Store™) that is achieved in methods for the extraction of total nucleic acid or targeted sequences. It was surprisingly discovered that nucleic acids can be screened and isolated from biological samples quickly, with sensitivity and with superior yields as compared to conventional procedures when using a methodology that combines MTM such as PrimeStore™ with magnetic capture using $SiO_2$ beads combined with carboxy magnetic beads (e.g., within a generated magnetic or electromagnetic field or with a magnet placed in sufficiently close proximity). In this embodiment, sample is collected in an MTM medium such as preferably PrimeStore™ to which is added magnetic capture material such as magnetic beads of, preferably, silica dioxide. Other types of beads are equally useful including glass beads and also magnetic materials that are not beads such as, for example, other magnetic matrix materials, resins and polymers. Total nucleic acid is captured by the magnetic materials and easily and quickly concentrated with a magnet, electro-magnetic field or other electrical field. Liquid may be removed and a second transition or intermediate buffer added designed to change pH in anticipation of a third buffer. This second buffer prevents clumping of cellular debris to the silica beads and releases the nucleic acids from the silica beads. Preferably the second or intermediate buffer has a pH of 7 or higher, of 8 or higher, or of 9 or higher and assist in the release of nucleic acids from the first matrix material. Preferably, the intermediate buffer functions synergistically with the third or binding buffer. The third buffer comprising preferably carboxy-modified magnetic matrix material and PEG/salt allow or encourage the binding of the released nucleic acids to the carboxy-modified matrix. The binding buffer plus the carboxy-modified matrix that are suspended serve a number of roles. A high salt component and presence of PEG reduce dielectric constant and enhance charge shield, respectively, which enable the negative phosphate backbone of RNA and DNA to bind to the net negative charge on the carboxyl terminus of the matrix material. This enhances efficient binding of minute concentrations of nucleic acids. Preferably the binding buffer includes a detergent (e.g., Tween-20, Triton-X), and NLS which promote further lysis and degradation of lipid bilayers. Also preferably the binding buffer contains ethanol which improves buffering viscosity and nucleic acid precipitation to the suspended matrix. Preferably, the binding buffer contain PEG (e.g., PEG-8000 at 15-20%), salt (e.g., NaCl at 1-2M), a buffering agent (e.g., Tris-HCl at 5-50 mM), detergent (e.g., Tween-20 at 0.01-0.1% and/or Triton-X at 0.01-0.10%), NLS (e.g., at 0.1-1.0%), an alcohol (e.g., ethanol at 15-30%), and matrix material (e.g., carboxy beads at 0.1 to 10.0 mg/ml).

In this embodiment, the nucleic acids are concentrated at two-fold or greater concentrations than when using traditional chromatography techniques, preferably five-fold or greater concentrations, more preferably ten-fold or greater concentrations, and more preferably twenty-fold or greater concentrations. Preferable the beads are coupled with an agent such as, for example, a carboxy group that specifically binds to a target nucleic acid sequence of interest.

Alternative, beads may contain modifications that bind to specific sequences. Such modifications may be chemical that promote binding between the bead and a certain chemical (e.g., A, G, C, T, U) or structural (e.g., lock and key binding). Modifications may comprise aptamers and/or specific sequences. Once bound, the beads, which are preferably magnetic, once again can be easily and quickly isolated and the target sequence eluted, which can be directly eluted into a nucleic acid detection assay such as, preferably, PCR, gene or whole genome sequencing, Ion Torrent Sequencing, Next Generation Sequencing and the like. As carboxy groups and most other chemical modifications of beads (e.g. modifications that create pendant groups) would be destroyed in PrimeStore™, the same beads can be used throughout the process—first to isolate all nucleic acids from the sample, wherein the carboxy functionality is not utilized, then to isolate specific nucleic acid sequences, wherein the carboxy functionality is utilized. Silica beads are also preferred for extraction step from PS and carboxy beads for the isolation of the target sequences. This process provides the additional advantage that the liquid from which the target nucleic acid was eluted remain intact and otherwise unaffected by any harsh or deleterious chemicals. Thus, the nucleic acids depleted of one target sequence can be re-analyzed for another, different target sequence. As the nucleic acids of the biological sample are returned to a stable condition with an MTM such as PrimeStore™, they can be re-used and re-tested repeatedly for the identification and isolation of many different target sequences of interest. A preferred method therefore involves placing the biological sample in PrimeStore, adding magnetic beads to couple with nucleic acids of the sample, isolating the beads and eluting the nucleic acid, adding additional magnetic beads but coupled with a carboxy group that specifically targets a nucleic sequence of interest, isolating those beads and eluting the target nucleic acid for subsequent DNA analysis such as PCR. The nucleic acid recover at each step is superior to conventional procedure and minimizes any need for a different solution or for different equipment at each step. Determining the amount or quantity of beads needed for each step can be determined from empirical information of determined experimentally.

Another embodiment of the invention is directed to systems whereby one or more biological samples are maintained in a MTM such as PrimeStore™ and subjected to an automated process that involves one or more cycles of isolation of targeted nucleic acid sequences. Optionally the very same MTM can be used throughout the process as can the very same beads, but for the beads used for targeting of specific nucleic acid sequences. High through-put devices can process many samples and detections simultaneously and with consistency, and without the inconsistencies that can be attributed to human error. This targeted process enriches the nucleic acids of the biological sample by removing a non-target sequence at each step. In other words, it becomes easier to identify and/or isolate each rare red marble from a background of many blue marbles by gradual elimination of the blue marbles.

Advantages of the preferred process of the invention utilizing PrimeStore™ and magnetic beads includes, but is not limited to faster processing and achievement of results, minimizing the number and complexity of steps and therefor associated costs. In addition, as PrimeStore™ can be utilized at ambient temperatures and contains no ingredients that would interfere with DNA testing, the entire process of identifying nucleic acid targets is simplified and streamlined.

The present invention also provides kits and sample collection systems utilizing the disclosed compositions and collection/storage/transport/isolation solutions described herein. In particular embodiments, such sample collection systems may include a collection device, such as a swab, curette, or culture loop; and a collection vessel, such as a vial test tube, or specimen cup, that contains one or more of the compositions disclosed herein. The collection vessel is preferably releasably openable, such that it can be opened to insert the one-step compositions and closed and packaged, opened to insert the sample and optionally a portion of the collection device and closed for storage and transport, or both. The collection vessel may use any suitable releasable or openable mechanism, including without limitation a screw cap, snap top, press-and-turn top, or the like. Such systems may also further optionally include one or more additional reagents, storage devices, transport devices, and/or instructions for obtaining, collecting, lysing, storing, or transporting samples in such systems. In a preferred embodiment, the one-step compositions of the invention may already be disposed in the reaction zone into which the sample may be associated. In such embodiments, the invention requires only a collection device and the collection vessel. The kit preferably includes one or more isolation or extraction elements to help liberate and/or separate one or more populations of nucleic acids contained within the sample from one or more other biomolecules or sample components to obtain at least partially, or substantially purified nucleic acids suitable for identification, detection, or further molecular analysis.

A preferred embodiment of the invention comprises compositions and methods comprising magnetic beads coated with a material that binds to RNA and/or DNA. These beads preferentially bind, for example, to MTB messenger RNA and/or DNA. Optionally, aliquots of the specimen in PrimeStore may be transferred to magnetic beads or filters to separate DNA from RNA. In one approach, mRNA or siRNA is filtered using size restricted filters. The DNA and/or RNA purified from PrimeStore is then detected with standard real-time PCR to MTB specific targets. A ratio of MTB RNA to DNA is analyzed to determine the change in viable MTB after therapy. Magnetic beads that bind RNA or DNA can be substituted for silica coated magnetic beads depending on the chemical composition of the binding solution. After the RNA or DNA are bound, they are eluted using an eluding solution and quantitated using real-time MTB specific PCR. One advantage of this approach is that the MTB are already lysed in the PrimeStore collection solution and specimen aliquots can go directly to filters or magnetic beads for either RNA or DNA isolation. This speeds the lab workflow for rapid MTB PCR RNA/DNA detection.

A preferred kit comprises beads suspended in a buffer for adherence/binding of RNA and/or DNA to bead surfaces for extraction of nucleic acids from biological samples. Preferably the buffer comprises components that do not alter the functionality of the beads, such as the functionality of carboxy beads. Preferably, components for a buffer do not include chaotropic agents, but includes agents to effectively bind nucleic acids (e.g., polyethylene glycol and NaCl) plus additional reagents and/or agents that are surfactants (e.g., Tween-20, Triton-X and ethanol and/or agents that promote further processing of cells and cellular debris (e.g., lysing, degradation of non-nucleic acid polymers).

Also, kits may be packaged for commercial distribution, and may further optionally include one or more collection, delivery, transportation, storage and/or isolation devices for sample or specimen collection, handling, or processing. The container(s) for such kits may typically include at least one vial, test tube, flask, bottle, cup, or other suitable container or collection device, into which the composition(s) may be placed, and, preferably, suitably aliquotted for individual specimen collection, transport, and/or storage. The kit may also include a larger container, such as a case, that includes the smaller, individual containers noted above, along with other collection devices, equipment, reagents, instructions, and/or the like. The kit may also optionally include one or more additional buffers, compounds, or compositions, and may also further optionally include one or more instructions detailing use(s) of the kit in either the collection or storage of one or more biological, clinical, diagnostic, environmental, or forensic sample. Optionally, the kit may also further provide instructions for the transport of the sample once placed in one or more of the disclosed compositions, and may even include instructions or additional reagents detailing one or more subsequent analytical methods or assays employing the nucleic acids isolated from the sample or specimen. Such kits may also include multiples of the various collection devices and collection vessels and any other components to be included, so that the kits can be used to collect multiple samples from the same source or different sources. In one commercial application, the kits are packaged in sets of five or more for convenient sale and use.

Optionally, compositions of the invention may include an appropriate detectable marker (i.e., a "label") for determining the presence of the nucleic acid of interest. A wide variety of appropriate indicator compounds and compositions are known in the art, including, without limitation, fluorescent, radioactive, enzymatic or other ligands, such as avidin/biotin, etc., which are capable of being detected. It may be desirable to employ a fluorescent label or an enzyme tag such as urease, alkaline phosphatase or peroxidase, instead of radioactive or other environmentally less-desirable reagents. In the case of enzyme tags, colorimetric, chromogenic, or fluorogenic indicator substrates are known that can be employed to provide a method for detecting the sample that is visible to the human eye, or by analytical methods such as scintigraphy, fluorimetry, spectrophotometry, and the like, to identify specific nucleic acids.

In general, probes described will be useful both as reagents in solution hybridization, as in PCR, for detection of particular nucleic acid sequences, as well as in embodiments employing a solid phase. One well-known amplification method is the polymerase chain reaction (referred to as PCR) which is described in detail in U.S. Pat. Nos. 4,683,195, 4,683,202 and 4,800,159, and each incorporated herein by reference in entirety. Another method for amplification is the ligase chain reaction ("LCR"), disclosed, e.g., in EPA No. 320 308, and U.S. Pat. No. 4,883,750, each of which is incorporated herein in its entirety by express reference thereto. Strand Displacement Amplification (SDA) is another method of carrying out isothermal amplification of nucleic acids that involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

The following examples illustrate embodiments of the invention, but should not be viewed as limiting the scope of the invention.

EXAMPLES

Once formulated, the stock solutions of PrimeStore™ are stable at 4° C. or below for periods of at least one year or more. Formulated PrimeStore™ solutions (PSSs) are stable at ambient temperature (e.g., about 20-30° C.) for periods of many months. Once a sample is contacted with a PrimeStore™ formulation, the mixture can be stored indefinitely at temperatures of 0° C. or below, at least one year or more under refrigeration (e.g., ≈4° C. and at least 30 days or more at ambient temperature (e.g., about 20-30° C.), without significant loss of nucleic acid composition, fidelity or integrity of the sample. For example, without limitation, the integrity of a population of polynucleotides obtained from the sample is at least substantially maintained, and preferably entirely maintained without detectable degradation, when the composition comprising the sample is stored at a temperature of from about minus 20° C. to about plus 40° C., for a period of from about 0 days to about 60 days or more.

Example 1—Formulation of Exemplary Storage Solutions

The present example provides a general formulation of the PSS compositions of the present invention. Additional formulations of the PSS compositions are exemplified in Examples 2 through 5.

Formulation Ranges of Exemplary Components for the Preparation of PrimeStore™ Compositions

| Compound | Final Concentration Range (examples) |
|---|---|
| A chaotrope, e.g.: | |
| Guanidine thiocyanate | about 0.5M to about 6M |
| and/or Guanidine hydrochloride | about 0.5M to about 6M |
| and/or Guanidine isocyanate | about 0.5M to about 6M |
| An anionic detergent, e.g.: | |
| N-lauroyl sarcosine (inter alia Na salt) | about 0.15% to about 1% (wt./vol.) |
| and/or Sodium dodecyl sulfate, | about 0.15% to about 1% (wt./vol.) |
| Lithium dodecyl sulfate, | about 0.15% to about 1% (wt./vol.) |
| Sodium glycocholate, | about 0.15% to about 1% (wt./vol.) |
| Sodium deoxycholate, | about 0.15% to about 1% (wt./vol.) |
| Sodium taurodeoxycholate, and/or | about 0.15% to about 1% (wt./vol.) |
| Sodium cholate | about 0.10% to about 1% (wt./vol.) |
| A reducing agent, e.g.: | |
| TCEP | about 0.05 mM to about 30 mM |
| and/or β-ME, DTT, formamide, or DMSO | about 0.05M to about 0.3M |
| 4. A chelator, e.g.: | |
| Sodium citrate | about 0.5 mM to about 50 mM |
| and/or EGTA, HEDTA, DTPA, NTA, APCA, etc. | about 0.01 mM to about 1 mM |
| A buffer (e.g., TRIS, HEPES, Bis-Tris, etc.) | about 1 mM to about 1M |
| An acid (e.g., HCl or citric acid) | q.s. to adjust to a pH of about 6 to 7, preferably about 6.8 to 7.0 |
| Nuclease-free water | q.s. to desired final volume |
| Optionally one or more of: | |
| A surfactant/defoaming agent, e.g.: | |
| Antifoam A ® or Tween ® | about 0.0001% to about 0.3% (wt./vol.) |
| An alkanol (e.g., methanol, ethanol, propanol, etc.) | about 1% to about 25% (vol./vol.) |
| A carrier/IPC RNA and/or DNA | about 1 pg to about 1 µg/µL |
| Magnetic NACM | about 1 ng to 10 mg per 1 mL |

Guanidine thiocyanate, sodium citrate, Antifoam A® Concentrate, and N-lauroylsarcosine, sodium salt, were all purchased from Sigma Chemical Co. (St. Louis, Mo., USA). Tris(2-carboxyethyl) phosphine hydrochloride (TCEP) was obtained from Soltec Ventures Inc. (Beverly, Mass., USA). 2-amino-2-hydroxymethyl-propane-1,3-diol (TRIS) was obtained from Applied Biosystems/Ambion (Austin, Tex., USA). 2-[2-(Bis(carboxymethyl)amino)ethyl-(carboxymethyl)amino]acetic acid (EDTA) GIBCO® Ultra Pure was obtained from Invitrogen Corp. (Carlsbad, Calif., USA). All other reagents are available commercially from Sigma-Aldrich or USB Corporation.

Example 2—Formulation of an Exemplary Storage Solution

The present example describes a first exemplary formulation of the compositions of the invention. This formulation is alternatively referred to as "PrimeStore™ Solution" or "PSS" version 1.

Preparation of PrimeStore™ Composition (Version 1)

| Compound | Final Conc. |
|---|---|
| Guanidine thiocyanate | 4M |
| Sodium citrate | 30 mM |
| Sodium dodecyl sulfate | 0.25% (wt./vol.) |
| N-lauroyl sarcosine, sodium salt | 0.25% (wt./vol.) |
| 2-mercaptoethanol (β-ME) | 0.1M |
| Antifoam A | 0.1% (wt./vol.) |

-continued

| Compound | Final Conc. |
|---|---|
| Citric acid | q.s. to adjust pH to 6.5 |
| Nuclease-free water | 11.82 mL |
| Magnetic NACM beads | 80 mg |

Example 3—Preparation of a Second Exemplary Storage Solution

The present example describes the preparation of another exemplary storage solution according to the present invention. This formulation may be referred to as PSS, which is PrimeStore™ version 2.

Preparation of PrimeStore™ Composition (Version 2)

| Compound | Quantity | Final Conc. |
|---|---|---|
| Guanidine thiocyanate | 35.488 gm | 3M |
| TCEP | 0.02867 gm | 1 mM |
| Sodium citrate | 0.2931 gm | 10 mM |
| N-lauroyl sarcosine, sodium salt (NLS) | 0.5 gm | 0.5% |
| Antifoam A (10% solution) | 200 µL | 0.002% |
| TRIS (1M) | 10 mL | 100 mM |
| EDTA (0.5M) | 20 µL | 0.1 mM |
| Hydrochloric acid (HCl) | q.s. to adjust pH to 6.9 | — |
| Nuclease-free water | q.s. to 100 mL | — |
| Magnetic NACM beads | 80 mg | 0.8 mg/mL — |

Example 4—Preparation of a Third Exemplary Storage Solution

The present example describes the preparation of another exemplary storage solution according to the present invention. This formulation is also referred to as PSS or PrimeStore version 2.2.

Preparation of PrimeStore™ Composition (Version 2.2)

| Compound | Quantity | Final Conc. |
|---|---|---|
| Guanidine thiocyanate | 29.574 gm | 2.5M |
| TCEP | 0.01434 gm | 0.5 mM |
| Sodium citrate | 0.2931 gm | 10 mM |
| N-lauryl sarcosine, sodium salt (NLS) | 0.4 gm | 0.4% |
| Antifoam A (10% solution) | 200 µL | 0.002% |
| TRIS (1M) | 10 mL | 100 mM |
| EDTA (0.5M) | 20 µL | 0.1 mM |
| Ethanol, molecular grade (96-100%) | 23 mL | 23% (vol./vol.) |
| Hydrochloric acid (HCl) | q.s. to adjust pH to 6.9 | — |
| Nuclease-free water | q.s. to 100 mL | — |
| Magnetic NACM beads | 80 mg | 0.8 mg/mL |

Example 5

The inactivation of gram-positive mycobacteria (e.g., inactivation of nucleases, sterilization of microorganisms) from sputum or other mucous-containing specimens that are contaminated with other organisms is difficult since mycobacteria are often shielded by the highly viscous sputum mucous content within the sample. The components present in PSS safely inactivate 10 concentrations of *mycobacterium* through chemical inactivation/killing by phospholipid membrane shearing, protein denaturation, chelation and buffering effect. However, mycobacteria present in collected primary sputum samples that contain human serum albumin, mucopolysaccharide and mucoprotein fractions may shield and protect the organism from direct inactivation by chemical inactivation mechanisms in PSS. Additional strategies to enhance mycobacteria inactivation from primary sputum samples collected in PSS include physical agitation using various sized porcelain, ceramic, plastic or glass beads. When combined with vortexing, the physical disruption of sputum matrix exposes the organism to PSS and facilitate greater inactivation. Furthermore, the same or different beads that are coated with silica dioxide and magnetized are used to bind and concentrate released DNA and RNA from inactivated cells and microbes though the chemical processes of PSS. The prerequisites for high affinity attachment of nucleic acid (DNA/RNA) to silica are: 1) a preferred pH of 6.8-7.0, and 2) a preferred presence of a chaotrophic agent. Both of these preferences are existing features of PSS formulation. PSS containing beads facilitates killing of mycobacteria in primary sputum samples. The further addition of magnetized, silica coated beads used in collection tubes and in combination with a magnetic stand concentrates nucleic acids from primary samples as well. In addition to physical agitation through bead-based vortex, the addition of heating (within a temperature range of 50-90° C.) and or sonication enhances inactivation and killing of mycobacteria in primary sputum samples.

Example 6 Exemplary Protocol for the Preparation of PSS 40 mL of nuclease-free water is first added to a clean beaker with a stir bar. The beaker is placed on a hot plate/stirrer and adjusted temperature to 60° C.-65° C. Stirring speed is set to medium and 29.574 gm of guanidine thiocyanate is added slowly to the water allowing it to dissolve as added. Next, 0.01434 gm of TCEP is added to beaker and stirrer speed increased to help dissolve crystals. 0.2931 gm of sodium citrate is added to the beaker followed by 0.4 gm of NLS to the solution. Stirrer speed is then increased again to create a vortex in the beaker. This vortex pulls the NLS into the solution and helps to dissolve reagent. A prepared 10% Antifoam A solution (1 mL Antifoam A Concentrate+9 mL nuclease-free water) is vortexed and 200 µL of the 10% Antifoam A is pipette into the solution. Next, 10 mL of 1 M TRIS is added into the solution and 20 µL of 0.5 M EDTA. Temperature is increased to bring the solution to 75-80° C. with stirring for 3-5 minutes. The beaker is removed from heat and the solution allowed to cool to room temperature (=22-25° C.). 23 mL of ethanol is added to the solution and mixed thoroughly, and the pH is adjusted to 6.9+/−0.1 with HCl. Solution is poured into a clean 200 mL graduated cylinder. 80 mg magnetic affinity matrix beads are added along with nuclease-free water to bring total volume to 100 mL. The solution is transferred to a labeled sterile container and stored at room temperature (=22° C.-25° C.). Preferably each reagent is completely dissolved before adding the next.

Example 7 Protocol for the Preparation of PrimeStore™ with Magnetic Beads Extraction PrimeStore MTM™ was prepared as a 1.5 mL solution in 3 mL cryovial tubes. Two types of commercially available silica coated, magnetized beads (MagAttract Material No. 1031699, Qiagen, and Agencourt, Beckman Coulter, Inc) were used for this example. A total of 100 µL of beads was added to PrimeStore MTM™ tubes. A purified strain of *Mycobacterium tuberculosis* (H37Rv) that was inactivated by gluteraldehyde and sonication was used at a concentration of $10^3$ CFU/mL. *Mycobacterium tuberculosis* (MTB)

was added to PrimeStore™ tubes containing magnetic beads and PrimeStore™ Tubes without magnetic beads (control). PrimeStore™ tubes were vortexed 5-10 seconds and tubes with beads were subsequently attached on top of a magnet for 2 minutes to attract tubes with beads to the bottom. While on the magnet, the PrimeStore™ tubes were uncapped and the solution was removed. Tubes were removed from the magnet and 200 µL of nuclease free water was added to the beads. Each tube was vortexed to elute nucleic acids from the beads. The PrimeStore™ tube was placed back on the magnet for 2 minutes to draw beads to the bottom. The eluate was transferred into a microcentrifuge tube. 200 µL of PrimeStore™ (without magnetic beads) containing MTB was removed and placed into a microcentrifuge tube to serve as an unconcentrated control. The 200 ul aliquots from bead-concentrated and control tubes were subjected to nucleic acid extraction using the Qiagen DNA Mini Kit (Qiagen Inc., Valencia, Calif.). Purified nucleic acids from both extraction procedures were amplified in replicate fashion using a real-time PCR assay on the ABI 7500 Real Time PCR System. Detection from PrimeStore MTM™ with magnetic beads had replicate $C_T$ values 28.50, whereas detection from PrimeStore MTM™ without magnetic beads had replicate $C_T$ values of 29.78. The decrease in $C_T$ values from samples that were concentrated using glass beads indicates a higher initial template starting concentration. These results demonstrate that silica coated beads and likely other affinity matrix materials as an example for any silica-coated matrix are compatible with PrimeStore MTM™ solution. Also, capture with magnetic beads allows an increase in concentration of nucleic acids from the sample prior to extraction, and enhances detection sensitivity. This allows for the concentration of nucleic acids from low-level samples for the potential detection of the presence or absence of pathogens in biological samples. Thus, the methodology is a simplified and efficient approach for concentrating minute quantities of nucleic acids (RNA and DNA) from collected specimens prior to extraction.

Example 8 Magnetized Beads with PrimeStore™ Molecular Transport Medium (MTM)

Magnetized bead types containing various surface coatings that include silica dioxide, heterogeneous silica derived molecules, glass fibers, polystyrene, and carboxyl-coated beads were evaluated with commercially available molecular transport medium for sensitivity in the capture of target DNA and/or RNA sequences. Commercially available magnetized beads are typically in the range of 0.5 to 10 micrometers (µM) in diameter. Additional sizes below and above this range are also commercially available and could be utilized. In addition to magnetized beads, other magnetized materials may be used. PrimeStore™ Molecular Transport Medium (MTM) (commercially available from Longhorn Vaccines and Diagnostics, LLC, Bethesda, Md.) promoted high affinity and reversible binding of the negatively charged phosphate backbone of RNA and/or DNA to silica-based surfaces. Reagents present in PrimeStore MTM™ (e.g., salts and guanidine-based compounds) coupled with a slightly acidic to neutral pH (i.e., pH 6.9) create the chemical environment needed for nucleic acid binding to silica-derived compounds. When silica is coated on the surface of magnetized beads and subsequently added at the proper concentration to tubes of PrimeStore MTM™, nucleic acids (RNA/DNA) of various sizes from collected samples are bound with high affinity.

Silica beads can be used synergistically with PrimeStore MTM™ for collection, transport, and processing of clinical, environmental, or laboratory strains for microbes including bacteria, eukaryotic, or viral cells and pathogens. Magnetized silica beads present in PrimeStore™ bind nucleic acids, and using simple magnetism or electromagnetism, the DNA/RNA bound to beads can be used to concentrate samples collected in PrimeStore MTM™ after decanting the liquid volume of PrimeStore™. Samples include the usual range of clinical, environmental, or laboratory-based cultures containing microbes of interest that are routinely collected in PrimeStore MTM™. Examples of clinical specimens include, but are not limited to, sputum, nasal washings, throat swabs, fecal material or urine, buccal, blood, serum, vaginal, or other bodily secretion. By concentrating samples in PrimeStore MTM™ containing magnetized, silica-coated beads prior to performing standard/routine nucleic acid extraction, a marked (10 to 100-fold) increase in the final extraction yields was seen as measured using quantitative real-time PCR.

Concentration step: A specimen is collected in PrimeStore MTM™ containing a concentration of silica-coated, magnetized beads. A magnet is applied to the base of the tube where beads containing all nucleic acids are bound. After a 1-2 minute magnet exposure, PrimeStore™ liquid is removed by decantation using a micropipette leaving 0.2 to 0.4 mL in the base of the tube. The magnet is removed and the remaining, now concentrated mixture of beads plus nucleic acids is pipetted directly to a commercial spin column for nucleic acid extraction (see FIG. 1).

In one example, the extraction yield of total genomic DNA from *Mycobacterium tuberculosis* was approximately 10 fold better when this concentration step was used prior to genomic DNA extraction compared to an equivalent volume that was not concentrated. In contrast to beads containing a silica dioxide coated surface, some commercial beads contain a core of polystyrene, one or more layers of magnetite, and a surface coating containing carboxylate (i.e., COOH). Carboxylate-coated beads are commercially available from several vendors including General Electric (GE) Health Care's SpeedBead Magnetic Carboxylate Modified Particles, Azide 0.05% (Part #65152105050250). Carboxylate beads placed directly in PrimeStore MTM™ did not bind nucleic acids, but have other utilities.

In one embodiment, a total nucleic acid carboxyl bead extraction kit including buffers optimized for binding, washing, and eluting can be utilized with specimens/samples that are routinely collected, shipped, and transported in Prime-Store MTM™. In this methodology, the developed nucleic acid extraction kit containing carboxylate beads and optimized buffers are compatible with PrimeStore MTM™ chemistry and used after sample collection. This is different from common extraction performed using a chaotrophic guanidine solution with silica dioxide spin columns (e.g., PrimeXtract, Qiagen spin columns, etc.) or silica magnetized beads (i.e., automated Roche MagnaPure™). An aliquot of 0.1 to 0.5 mL of sample/specimen collected in PrimeStore™ is added to an optimized buffer containing but not limited to: polyethylene glycol (PEG), sodium chloride or other salts or combinations of salts, Polysorbate 20 or other surfactants/detergents, TRIS or other buffering agents, EDTA or other preservatives, that are optimized at the proper molar concentrations to synergistically work with PrimeStore™ MTM such that the ratio of added Prime-store™ plus sample to carboxyl bead buffer promotes nucleic acid binding to carboxyl beads.

In another embodiment, a target specific nucleic acid carboxyl bead extraction kit including buffers optimized for binding, washing, and eluting can be utilized with specimens/samples that are routinely collected, shipped, and transported in PrimeStore MTM™. For example, chemically modified carboxy beads containing highly conserved influenza sequences are used to capture minute concentrations of influenza virus RNA from clinical nasal washings or throat swab specimens in PrimeStore MTM™. While viral RNA levels are contingent on the quality of the collected patient specimen, the extraction yields improved by a highly specific "target capture" methodology that binds the minute RNA of choice and removes all other nucleic acids from the final elution. In other words, the ability to capture a specific sequence is improved by reducing the majority of non-specific sequences that are also present.

Figure 2:
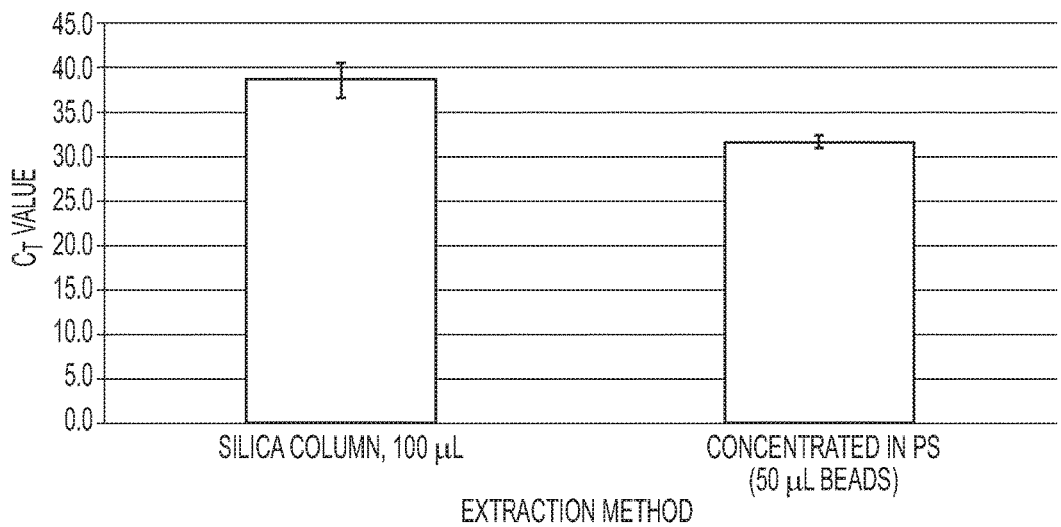
FIG. 2 Extraction using a concentration step with beads in PrimeStore™ from low-level MTB sample at $10^1$ CFU/ml.

Another embodiment of the invention involves a combinational use of bead types that work synergistically to: (a) concentrate total nucleic acids from a sample thus removing unwanted proteins, carbohydrates, lipids, and other inhibitory compounds/reagents, and then (b) targeting/capturing a specific nucleic acid sequence, or set of sequences. In this approach, specimens are collected in PrimeStore MTM™ by routine methodology. The sample is concentrated using silica beads present in PrimeStore™ by magnet capture and the remaining liquid volume discarded. Beads with bound nucleic acids are washed and/or eluted using an elution buffer. The elution containing total nucleic acids is added to a buffered solution containing modified carboxylate beads containing highly conserved, hybridization oligonucleotides for capture of specific genomic DNA (gDNA), mRNAs, siRNA, viral RNAs (vRNA) or other nucleic acid targets. An experiment comparing the extraction from a silica column to extraction with PrimeStore™ (PS) plus magnetic beads is shown in FIG. 2 and summarized below.

Low-Level Concentration with Beads in Primestore™

| MTB Extraction Method | MTB Target (Triplicate $C_T$ avg.) | | | | |
|---|---|---|---|---|---|
| Silica Column, 100 μl | 38.8 | | | | |
| Concentrated in PS (50 μl Beads) | 32.3 | | | | |

| | MTB 6110 Assay | | | | |
|---|---|---|---|---|---|
| MTB Extraction Method | $C_T$ Values | | | Avg. | Std. Dev. |
| Silica Column, 100 μl | 40.0 | 36.5 | 40.0 | 38.8 | 2.02 |
| Concentrated in PS | 31.9 | 32.9 | 32.1 | 32.3 | 0.67 |
| (50 μl Beads) | 31.6 | 32.7 | 32.8 | | |

As depicted in FIG. 2, this methodology is highly advantageous for applications that rely on highly purified target sequences derived from low-level clinical specimens. For example, whole genome sequencing (WGS) from microbes procured directly from clinical specimens, e.g., *Mycobacterium tuberculosis* from sputum.

Figure 3:
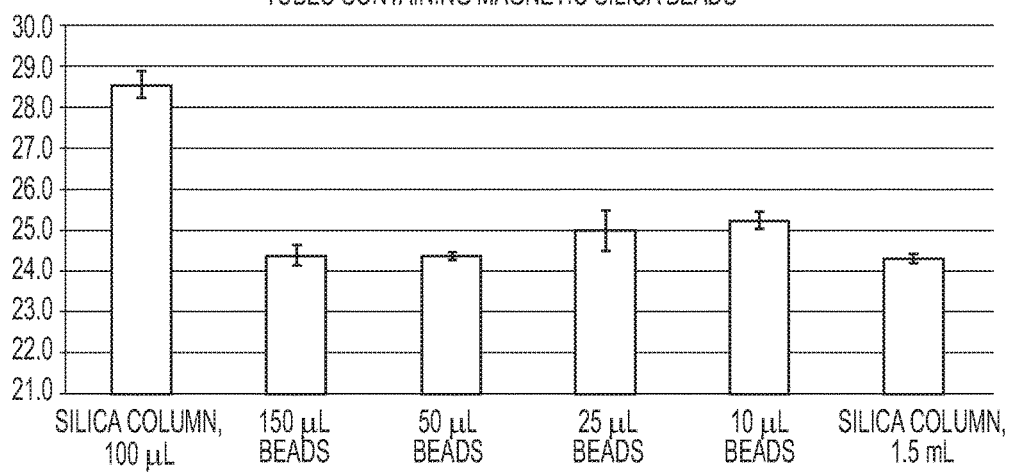
FIG. 3 Concentrating nucleic acids directly from PrimeStore MTM™ tubes containing magnetic silica beads.

100 μL of 10-2 diluted Stock MTB (gluteraldehyde-fixed) from Battelle Inc. was pipetted into PrimeStore™ (DNA) tubes containing 1.5 mL of volume. Shown in FIG. 3 are PrimeStore MTM™ tubes (containing a varying bead concentrations) that were concentrated using a simple magnet prior to spin column extraction. Using a magnet approximately 1.1 mL of PrimeStore MTM™ was removed with a remainder of ~400 μL in the tube. The concentrated 400 μL volume containing beads with bound DNA/RNA was transferred directly from PrimeStore™ tubes into a silica spin column for extraction. In all experiments 400 μL was extracted by silica spin columns and eluted in 50 μL of nuclease-free water. Results depicted in FIG. 3 are summarized below.

Concentrating Sample Using Silica Beads in Primestore™ Prior to Extraction

| MTB Extraction Method | MTB Target (Duplicate $C_T$ avg.) | | | |
|---|---|---|---|---|
| Silica Column, 100 μl | 28.6 | | | |
| 150 μl Beads | 24.4 | | | |
| 50 μl Beads | 24.5 | | | |
| 25 μl Beads | 25.1 | | | |
| 10 μl Beads | 25.4 | | | |
| Silica Column, 1.5 ml | 24.5 | | | |

| | MTB Assay | | | |
|---|---|---|---|---|
| MTB Extraction Method | $C_T$ Values | | Avg. | Std. Dev. |
| Silica Column, 100 μl | 28.3 | 28.8 | 28.6 | 0.33 |
| 150 μl Beads | 24.6 | 24.3 | 24.4 | 0.24 |
| 50 μl Beads | 24.4 | 24.5 | 24.5 | 0.07 |
| 25 μl Beads | 25.5 | 24.8 | 25.1 | 0.49 |
| 10 μl Beads | 25.2 | 25.5 | 25.4 | 0.22 |
| Silica Column, 1.5 ml | 24.6 | 24.4 | 24.5 | 0.11 |

The gold standard comparator (indicated as "Silica Column, 1.5 ml"; FIG. 3) is an extraction of the entire 1.5 mL of PrimeStore™ solution containing MTB through the filter column by multiple passages. Indicated as "Silica Column, 100 μl" (FIG. 3) is extraction from PrimeStore MTM™ containing no beads. Thus, using multiple passages the maximum nucleic acid recovery according to qPCR cycle threshold ($C_T$) values is 24.5 compared to 28.6 when only 100 μL is extracted. Magnetized silica coated beads effectively concentrated the recovery of nucleic acids as indicated by $C_T$ values in real-time PCR (indicated as "150 μl Beads"; "50 μl Beads"; "25 μl Beads"; "10 μl Beads"; FIG. 3). The PrimeStore MTM™ tube containing 50 μL of beads was optimal and showed a 24.5 $C_T$ value indicating comparable recovery compared to control (indicated as Silica Column, 1.5 ml). Importantly, there is 4.1 $C_T$ difference or greater than 10-fold improvement when samples are concentrated prior to extraction (compare bar shown as "Silica Column, 100 μl" with bars shown as "150 μl Beads"; "50 μl Beads"; "25 μl Beads"; "10 μl Beads"; FIG. 3).

Figure 4:
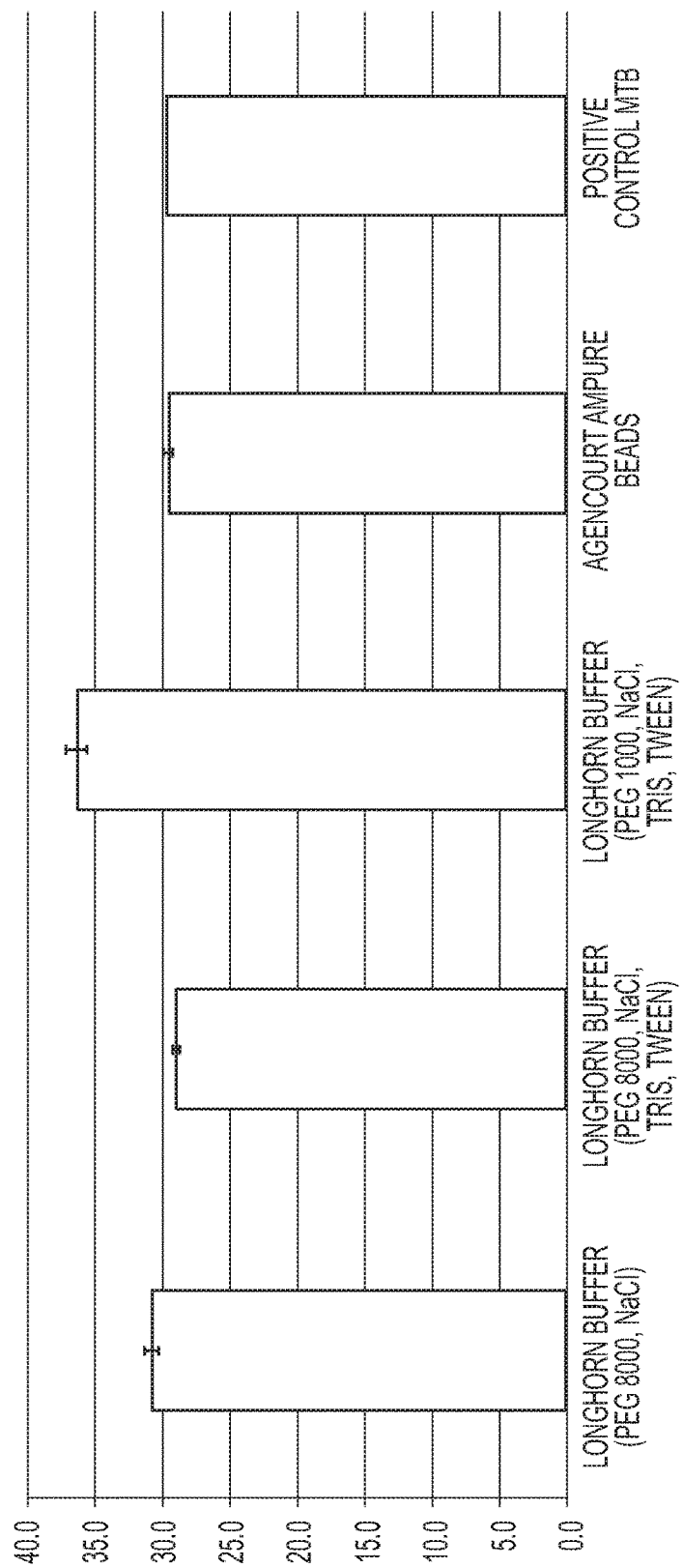
FIG. 4 MTB nucleic acid purification using magnetic beads in buffer formulations compared to AgenCourt buffer/beads.

In a next experiment, a formulated carboxy-friendly buffer was compared to the proprietary buffer that Agencourt uses in its AMPure bead solution. To accomplish this, three formulations were designed at LH (designated as "Longhorn Buffers"). An equal amount of total genomic MTB DNA ($10^4$ CFU/mL) was added (1:2 ratio of MTB:Beads) to the buffer/bead mixture, cleaned with 80% ethanol, and eluted in 50 μL of water. A positive control MTB reaction (indicated as "Positive Control, MTB"; FIG. 4) containing the exact concentration of MTB was used as the "best case" control to compared to the test reactions. Results depicted in FIG. 4 are summarized below.

Comparison of Buffers/Beads

| MTB Extraction Method | MTB Target (Duplicate $C_T$ avg.) |
|---|---|
| Longhorn Buffer (PEG 8000, NaCl) | 30.9 |
| Longhorn Buffer (PEG 8000, NaCl, Tris, Tween) | 29.1 |

-continued

| | |
|---|---|
| Longhorn Buffer (PEG 1000, NaCl, Tris, Tween) | 36.5 |
| Agencourt AMPure Beads | 29.7 |
| Positive Control MTB | 29.8 |

| | MTB 6110 Assasy | | |
|---|---|---|---|
| MTB Extraction Method | $C_T$ Values | Avg. | Std. Dev. |
| Longhorn Buffer (PEG 8000, NaCl) | 31.2  30.5 | 30.9 | 0.49 |
| Longhorn Buffer (PEG 8000, NaCl, Tris, Tween) | 29.1  29.0 | 29.1 | 0.07 |
| Longhorn Buffer (PEG 1000, NaCl, Tris, Tween) | 35.9  37.0 | 36.5 | 0.78 |
| Agencourt AMPure Beads | 29.5  29.8 | 29.7 | 0.21 |
| Positive Control MTB | 29.8 | 29.8 | |

The Longhorn Buffer containing 8000 PEG and other reagents was equivalent to the Agencourt AMPure bead buffer mixture. The carboxy beads used were provided by GE Healthcare.

Figure 5:
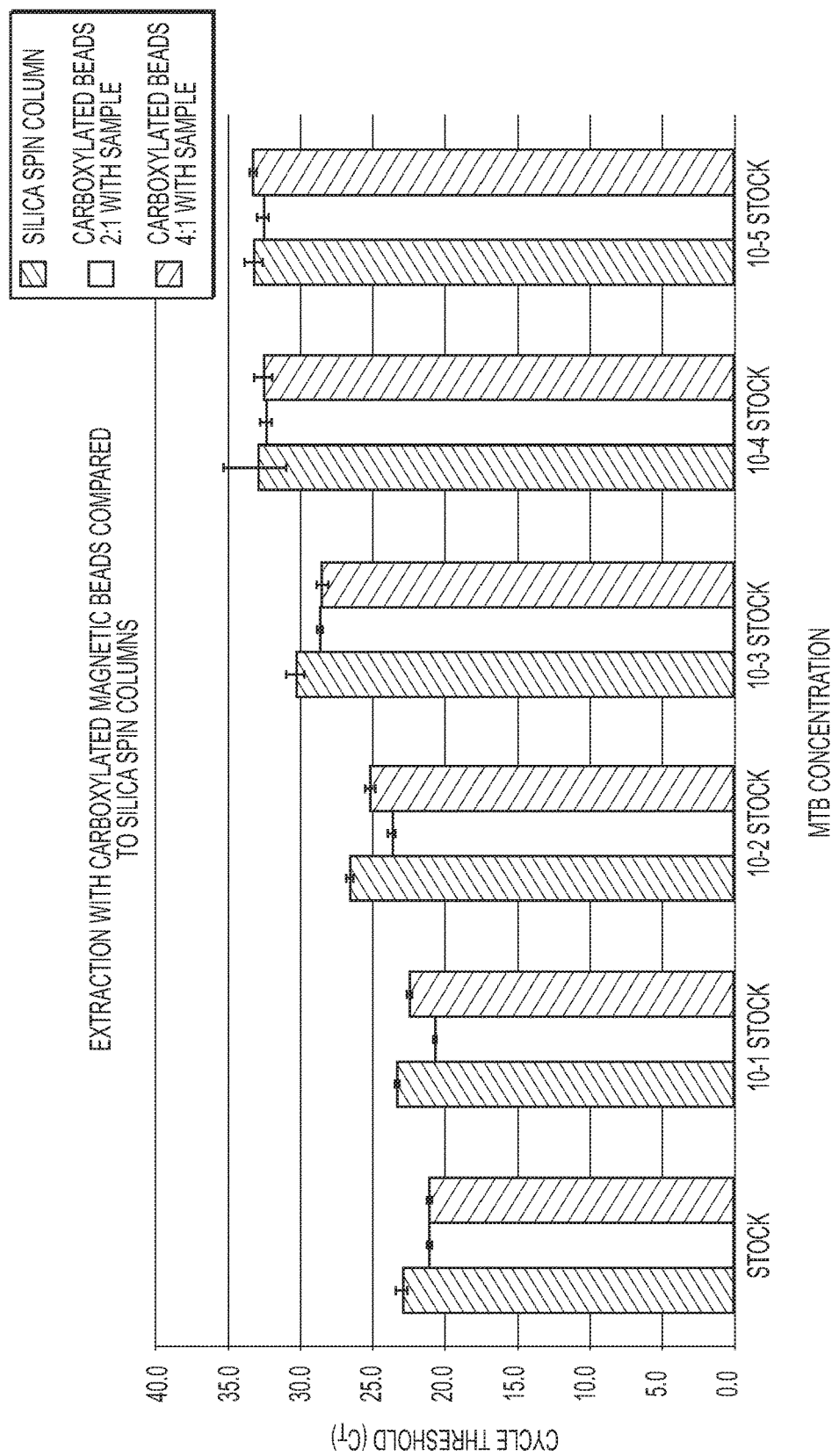
FIG. 5 Extraction with carboxylated magnetic beads in comparison with extraction from silica spin columns.

Example 9 Extraction with Carboxylated Magnetic Beads Vs. Silica Spin Columns FIG. 5 shows two surprising findings. First, PrimeStore MTM was determined to be compatible with carboxy beads/optimized buffer. The pathogen used was *Mycobacterium tuberculosis* in clinical samples, which was placed in PrimeStore MTM and then extracted using a buffer with magnetized, carboxy beads. In FIG. 5, the first bar of each MTB concentration shows the cycle threshold (Ct) when using spin columns for extraction (BLUE diagonal stripes). The second bar depicts Ct for carboxylated beads at a concentration with sample of 2:1 (RED, no stripes). The third bar depicts Ct for carboxylated beads at a concentration with sample of 4:1 (GREEN horizontal stripes). The MTB concentration used was stock, 10^-1 dilution of stock, 10^-2 dilution of stock, 10^-3 dilution of stock, 10^-4 dilution of stock and 10^-5 dilution of stock. The lower Ct achieved with carboxylated beads in buffer as compared with Ct values from spin columns demonstrate increased detection. The buffer comprised PEG-8000 at 15.68%, NaCl at 1.96M, Tris-HCl at 8 mM, EDTA at 0.8 mM, Tween-20 at 0.08%, Tritin-X at 0.08%, MLS at 0.32%, and ethanol at 20%, which when included, contained carboxy beads at 1 mg/ml.

Surprisingly, when compared with extraction of these same samples using silica spin columns, the overall extraction performance for carboxy-bead extraction was slightly better across a 6-log dynamic range of titered pathogen compared to standard, widely used spin column purification using silica columns.

Example 10 Carboxy Bead Extraction

Buffer D was prepared in 100 mL conical tube with 49 mL PEG-8000/NaCl (2.5M NaCl and 20% PEG) (final conc. 15.68%), 0.5 mL 1 M Tris-HCL (final conc. 1.96M), 0.1 mL EDTA (final conc. 8 mM), 50 µL of Tween-20 (final conc. 0.08%), 50 µL of Triton-X (final conc. 0.08%), 0.2 grams NLS (final conc. 0.32%), 12.5 mL of 100% Ethanol (final conc. 20%), and 0.4 mL of GE carboxy beads suspended in TE (10 mM Tris-HCl, 1 mM EDTA) prepared by cleaning 1 mL of fully mixed stock GE beads (50 mg/mL), and washing 3× with magnet and TE buffer or purified water. Re-suspend the 50 mg of Stock GE beads in 0.4 mL of TE buffer and add to prepared buffer D. To make Adenovirus/PrimeStore dilutions (thereby simulating nucleic acids of a biological sample but standardized for comparative purposes), whole Adenovirus culture was diluted 1.0 mL into 9.0 mL of PrimeStore and serially diluted from $10^{-1}$-$10^{-8}$ dilutions. Stock Adenovirus was not used for these experiments. 200 uL of each Adenovirus dilution was placed in a series of 1.5 mL microcentrifuge tubes. Depending on the type of extraction method, 200 uL spin column, 300 uL Saline-Life Tech 600 uL GE or ReSyn carboxybeads were used in singlets to test for extraction efficiency. With the spin column methods, the initial 'soup' of adenovirus sample in PrimeStore and lysis/EtOH was centrifuged through at 600 uL (200 uL sample+400 uL 'soup') until all was passed. The wash steps: 1 and 2 were under normal protocols at 200 uL each, with wash 2 twice to ensure efficient purification. The elution step was carried out with two hot 25 uL aliquots centrifuged twice to ensure maximum yield.

For the bead extractions, the beads were prepared by washing 0.5 mL of stock Saline beads (Part#: 37002D) three times in nuclease-free water and re-suspended in 25 mL of PrimeXtract Lysis Buffer. This dilution gives a final silica bead concentration of 0.8 mg/mL. The Buffer D formulation+carboxy beads was made by taking 1.0 mL of Stock beads (50 mg/mL) and placing it in 50 mL of Buffer D after washing the beads three times in TE Buffer. This dilution gives a final carboxy bead concentration of 1 mg/mL.

For Saline bead only extractions, 300 uL of beads were added to a 1.5 mL low-bind microcentrifuge tube. 200 uL of serially diluted infused PrimeStore was added and allowed to vortex/incubate for 5 minutes. PrimeXtract wash 1 and 2 were added in 200 uL amounts with wash 2 occurring twice to increase extraction purity. A heated step was added for 30 seconds to ensure complete ethanol removal. 50 uL nuclease-free water (heated) elution was added and allowed to incubate for 1 minute. The elution volume was transferred to a new 1.5 mL microcentrifuge tube.

To each PrimeStore diluted Adenovirus tube (set of 1), 300 uL of prepared beads (Saline) was added directly to 200 uL of serially diluted Adenovirus in a low-bind microcentrifuge tube, the solutions were constantly vortexed/incubated for 5 minutes. A magnet stand was used to sequester the beads on the side while the liquid volume inside the tube was aspirated. The beads were resuspended in 200 uL freshly prepared NALC solution (alkaline pH). The slurry beads were incubated for 10 minutes then vortexed and allowed to incubate for 5 minutes all at room temperature (e.g., ambient temp.). Once complete, the slurry was sequestered by the magnet stand and 600 uL of carboxy beads (GE Healthcare or ReSyn in Buffer D) was added to the remaining volume of liquid to allow for nucleic acid transfer. The new combination of beads was vortexed and incubated for 5 minutes.

The beads were sequestered using a magnet stand and the fluid volume was aspirated using a pipette. Two washes of freshly made 80% EtOH were added (500 uL each) and each time aspirated using the magnet stand. A hair dryer heated step (heat reduces the drying time, but is not otherwise required) was added for 30 seconds to ensure complete ethanol removal (residual EtOH interferes with PCR) and elution was carried out by adding 50 uL of hot nuclease free water to the beads and incubating for 1 minute. Elution volumes were transferred to new 1.5 mL collection tubes for real-time PCR Adenovirus assay in double repetitions to test for extraction efficiency.

Figure 6:
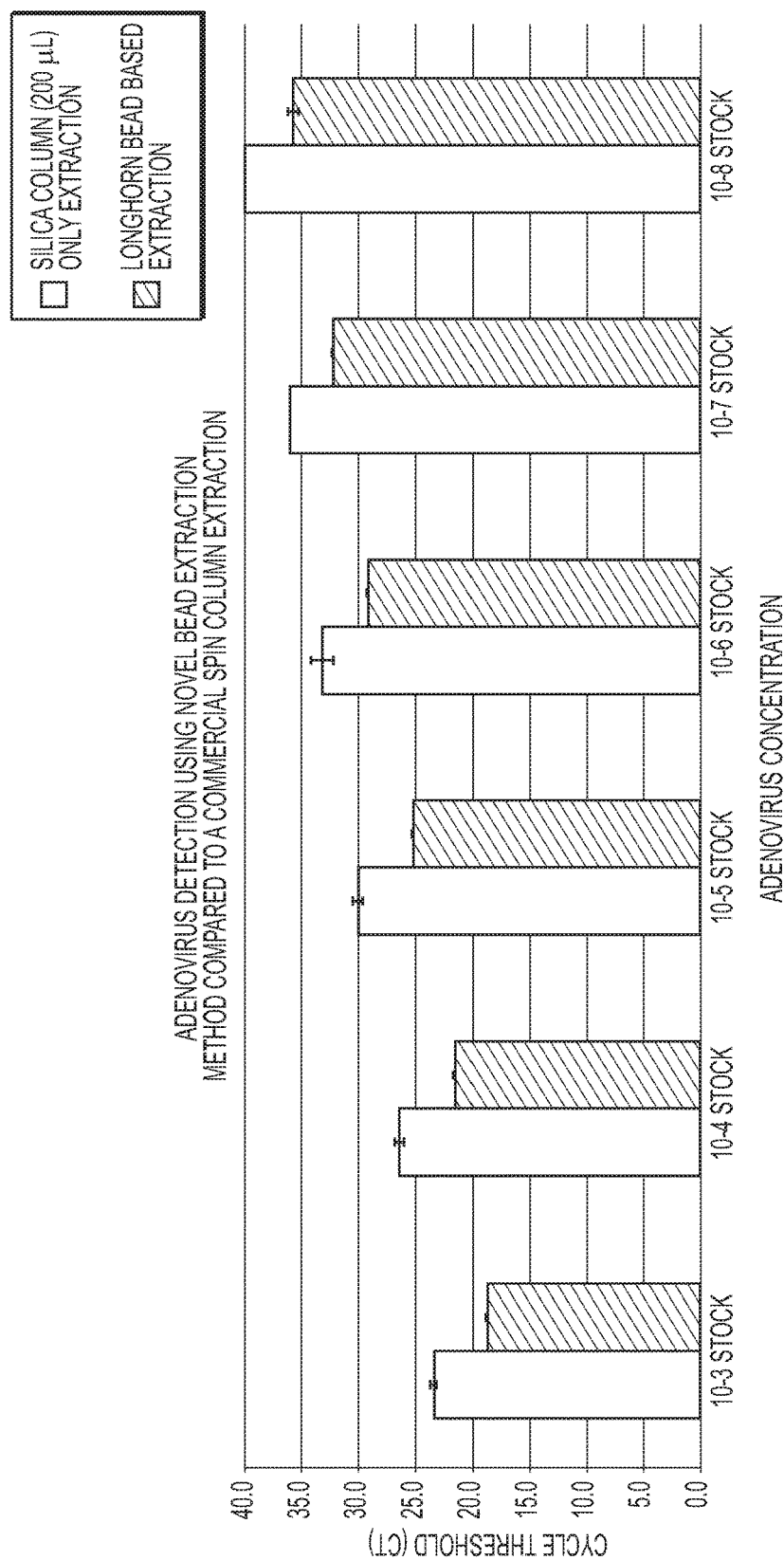
FIG. 6 Adenovirus detection using bead extraction method compared to spin column extraction.

Briefly, a three-step approach is used as a bead-based extraction system. Step 1 involves concentrating a 2.0 mL samples of adenovirus collected in PrimeStore MTM (across a 10-fold serial dilution). This was performed using commercially available silica coated beads (Life Technologies). The beads are magnetized so concentration was performed with a magnet and the liquid volume (in this case PrimeStore MTM (Longhorn Vaccines and Diagnostics, LLC) and lysed cellular debris) removed from the tube. Step 2) An intermediate buffer (e.g., Tris-HCl/NaOH, saline, dilute alkaline, TE buffer, and/or NALC) was added to the sample with a basic pH as a compatible matrix for the addition of magnetized carboxy beads. This intermediate buffer also emulsifies difficult specimens such as sputum, nasal discharge, tissues, etc. which can create a slime-like coating on the beads. The solution prevents the beads from clumping and further chews up difficult samples. Step 3) carboxy beads in Buffer D were added to the tubes. Buffer D does not contain chaotrophic agents (e.g., guanidine) or denaturing agents, but contains PEG (polyethylene glycol and NaCl) to effectively precipitate and dehydrolyze nucleic acids; plus additional surfactants (e.g., Tween-20, Triton-X) and ethanol that promote further processing (lysing, degradation of non-nucleic acid polymers) of cells and cellular debris. As shown in FIG. 6, superior detection was noted using this three-step approach compared to commercial extraction using silica spin columns across every dilution. Most surprising, was that at the lowest dilution (adenovirus at $10^{-8}$, about 10 genomic equivalents), spin columns had a $C_T$ value of 40 (no detection) while we showed detection at a $C_T$ value of 35. FIG. 6 demonstrates superior detection, as evidenced by decreased cycle threshold values ($C_T$) during real-time PCR with bead-based extraction (second column, diagonal stripes), as compared to results obtained using a routine commercial silica column extraction kit (first column, no stripes).

Example 11 Carboxy Bead Extraction Using Different Sources of Beads

Figure 7:
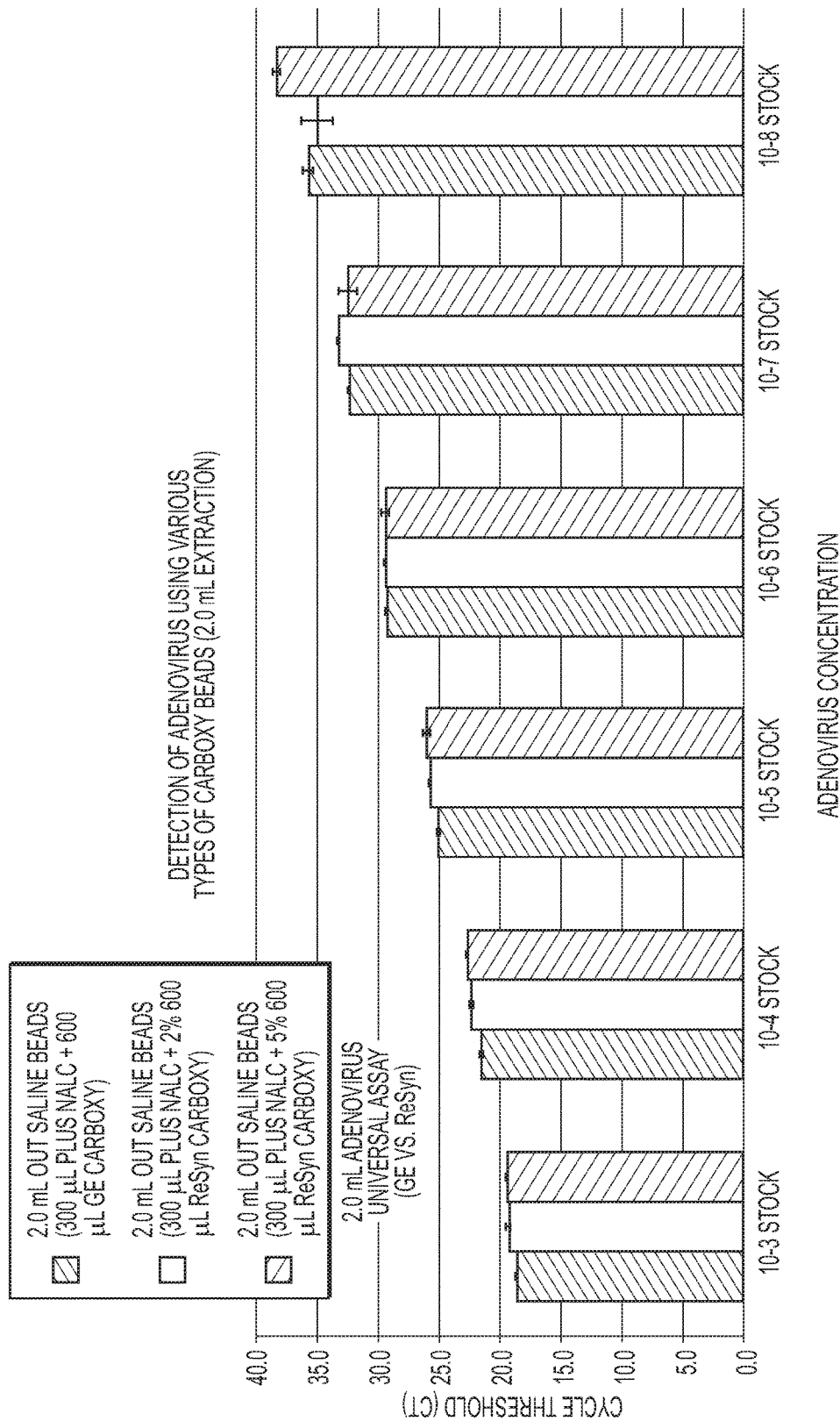
FIG. 7 Detection of Adenovirus using different types of carboxy beads.

FIG. 7 shows the results of carboxy bead extraction with three different compositions of commercially available carboxy beads (all OUT saline beads, 300 µl plus NALC). Triplicate real-time PCR reactions were analyzed over a range of $10^{-3}$ to $10^{-8}$ using a real-time universal Adenovirus assay. The first column of each set represents the cycle threshold achieved with carboxy beads obtained from GE (Cardiff, Whales) (RED diagonal stripes with 600 µl GE carboxy. The second and third column of each set are Resyn beads (South Africa) at 2% (BLUE no stripes with 2% 600 µl ReSyn Carboxy) and 5% (GREEN horizontal stripes with 5% 600 µl ReSyn Carboxy) respectively. This example illustrates that different types of carboxy beads provide the similar results. Although beads provided by GE Healthcare had slightly superior performance (lower Ct value), there were little difference between bead brands used.

Example 12 MTB Detection Using Real-Time PrimeMix MTB Multiplex Assay

Figure 8:
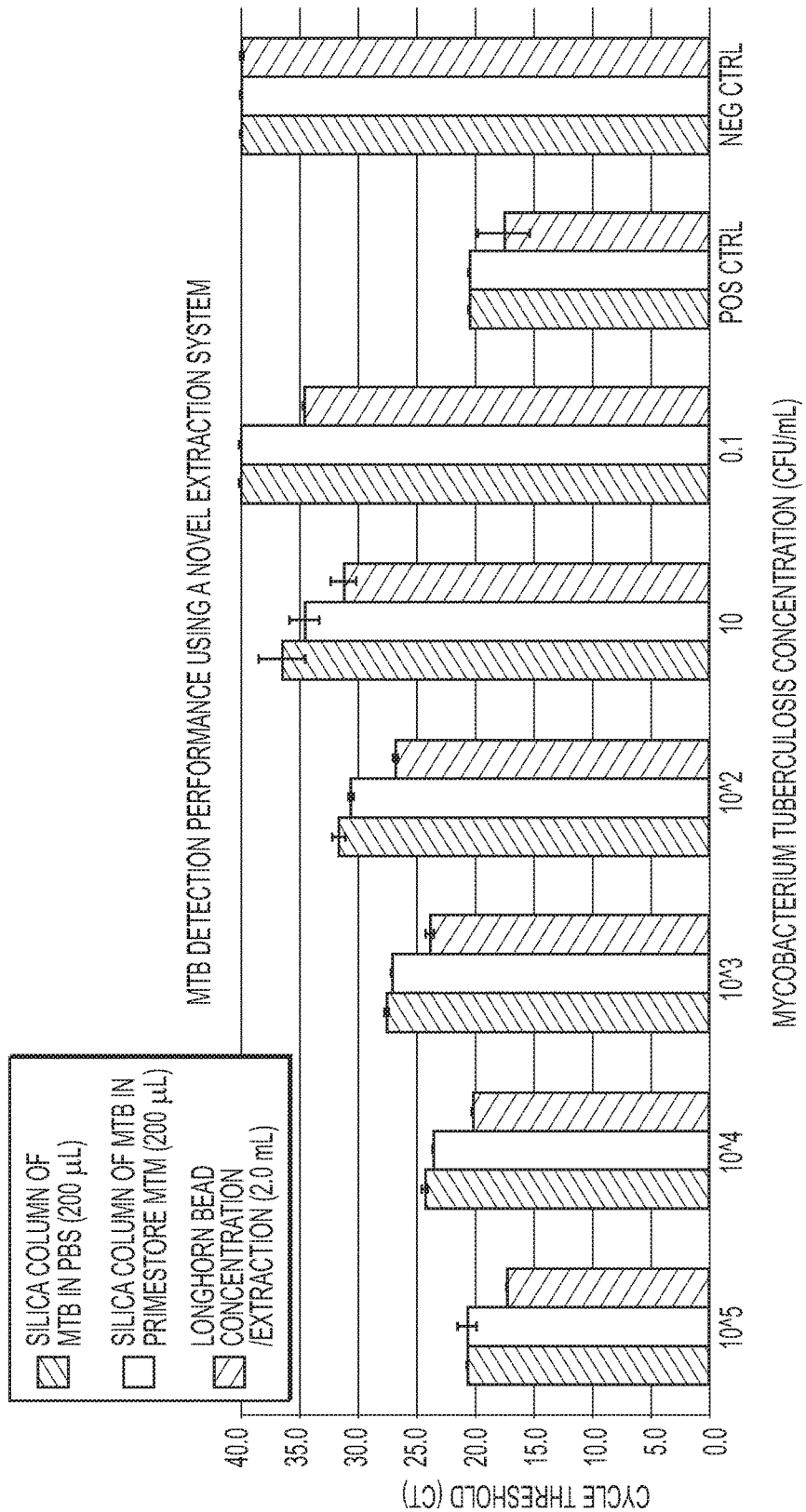
FIG. 8 Ten-fold serial reduction of glutaraldehyde fixed whole *Mycobacterium tuberculosis* (MTB) detection using real-time PrimeMix MTB Multiplex assay.

A comparison of a standard commercial silica column extraction from two 10-fold serial reduction ladders of MTB in either PrimeStore Molecular Transport Medium (MTM; Blue, no stripes) or phosphate buffered solution (PBS; Red, diagonal stripes) is shown in FIG. 8. As can be seen, MTB placed into PrimeStore MTM was more sensitive (based on real-time PCR cycle threshold values) compared to equivalent amounts of MTB in PBS, which is considered a benign matrix. This difference is believed due to the ability of PrimeStore to completely lyse the phospholipids of gram-positive bacteria, even the very hardy MTB microbes. At the lowest dilution (0.1 CFU/mL) there was no detection ($C_T$=40) for both MTB in PrimeStore and PBS. However, when MTB was extracted using a bead-based approach developed at Longhorn that involves first concentrating 2.0 mL and then extracting using a combination of silica and carboxy beads, the lowest dilution was readily detected ($C_T$=34; Green, horizontal stripes). This is significant because common or routine silica spin column extraction methods would not be able to detect pathogen target from low-level samples, particularly from original specimens (sputum, nasal washings, etc.) where loads may be below detection limits. The ability to concentrate and extract using the bead-based approach described herein increases detection/characterization limits using downstream molecular methods such as real-time PCR and/or next-generation sequencing.

Previously this approach was demonstrated for detection of adenovirus. This application uses *Mycobacterium tuberculosis*, and can be expanded for use in HIV viral load detection or for detection of influenza viruses. Furthermore, this chemistry and described methodology involves magnets and magnetized nanobeads and can be adapted for use in automated extraction units such as the Roche MagnaPure, Qiagen M48 and other commercially available systems.

Example 13

Figure 9:
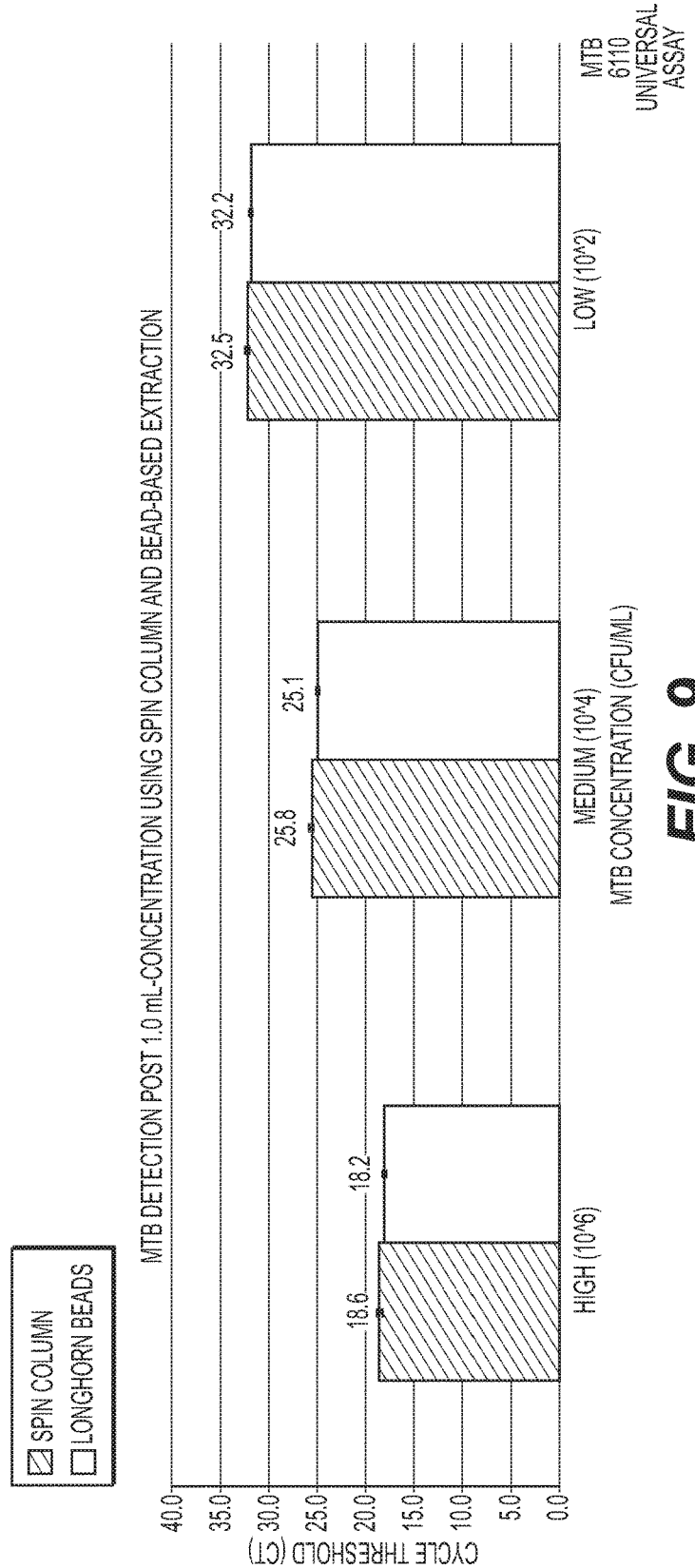
FIG. 9 MTB detection post 1.0 ml concentration using spin-column and bead-based extraction.
Figure 10:
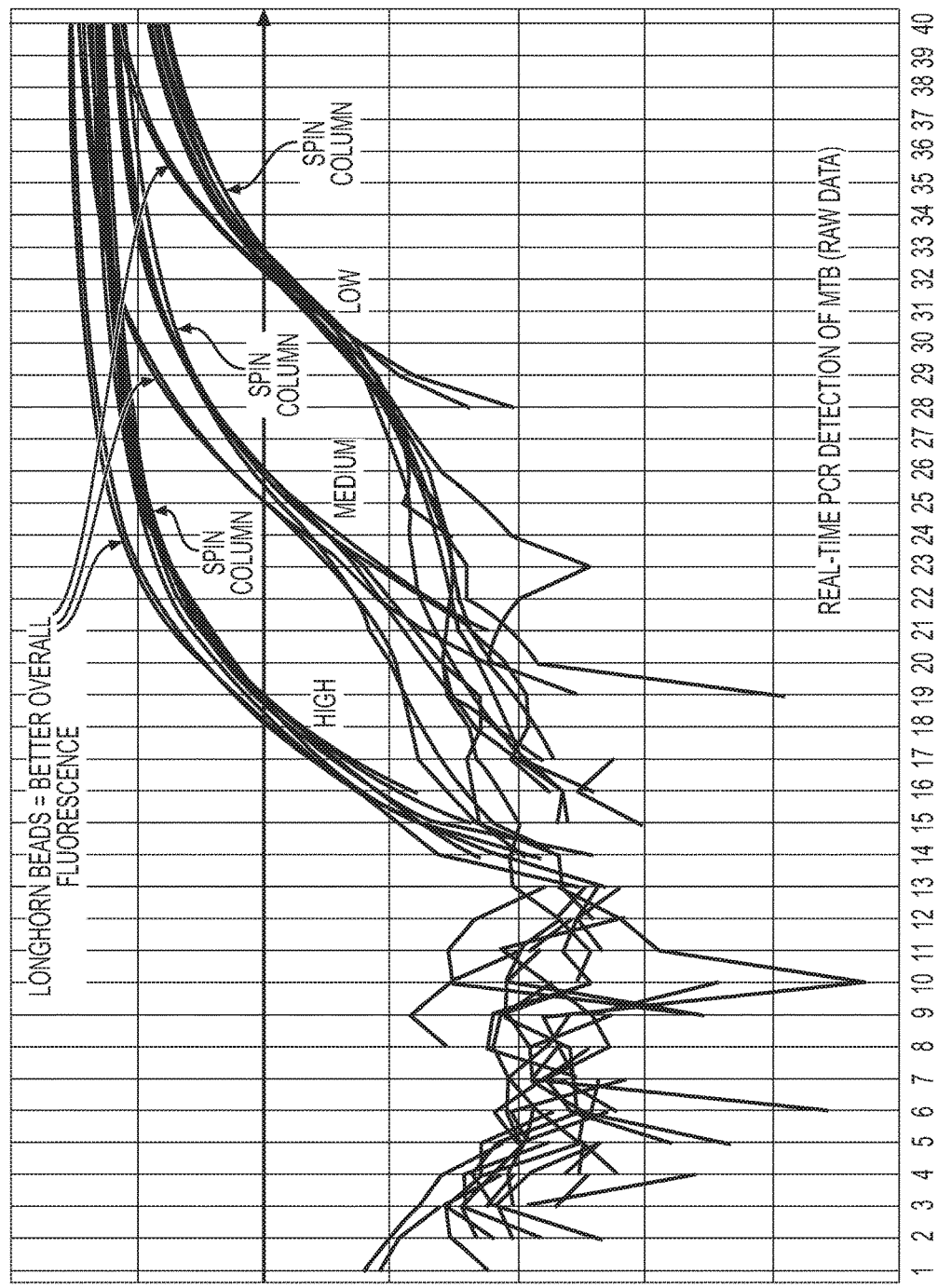
FIG. 10 Real-time PCT detection of MTB.

Real-time PCR detection using PrimeMix MTB Complex after concentrating total nucleic acids from MTB in PrimeStore MTM (i.e., high, medium and low concentrations). As shown in FIG. 9, after concentrating 1.0 mL down to ~0.1 mL, samples were extracted using: 1) commercial spin column (PrimXtact) extraction (RED, diagonal lines), or 2) Longhorn's bead-based methodology (GREEN, no lines). According to quantitative real-time PCR detection of high, medium, and low MTB concentrations spin column and bead extraction methods were comparable when processed after an initial concentration step. However, the Longhorn bead based method showed slightly better cycle threshold values at all three concentrations. Triplicate averages are shown. After first performing concentration step using silica beads, one can either continue with extraction using the carboxy bead methodology disclosed herein or a conventional spin column extraction methodology. From the raw dataset, repeated samples show that overall fluorescence was slightly better using Longhorn beads compared to silica spin columns (see FIG. 10; high, medium and low refer to FIG. 9 values). This indicates a cleaner preparation with less carryover of contaminates.

Example 14

The extraction procedure was developed using optimized buffers and chemically coated magnetized beads for concentrating and subsequently purifying nucleic acids from samples collected in PS-MTM to enhance quantitative PCR (qPCR) microbial detection.

Ten-fold serial dilutions of influenza A H3N2 ($10^5$ to $TCID_{50}$/ml), and *Mycobacterium tuberculosis* (MTB; $10^5$ to 1 CFU/ml) were prepared in PS-MTM and analyzed using an ABI-7500 instrument. Prior to amplification triplicate nucleic acid extractions were performed for each dilution using bead-based extraction and compared to commercial extraction using Qiagen QiAmp DNA Mini. An experimental overview of the methodology is shown in FIG. 11.

Figure 12A:
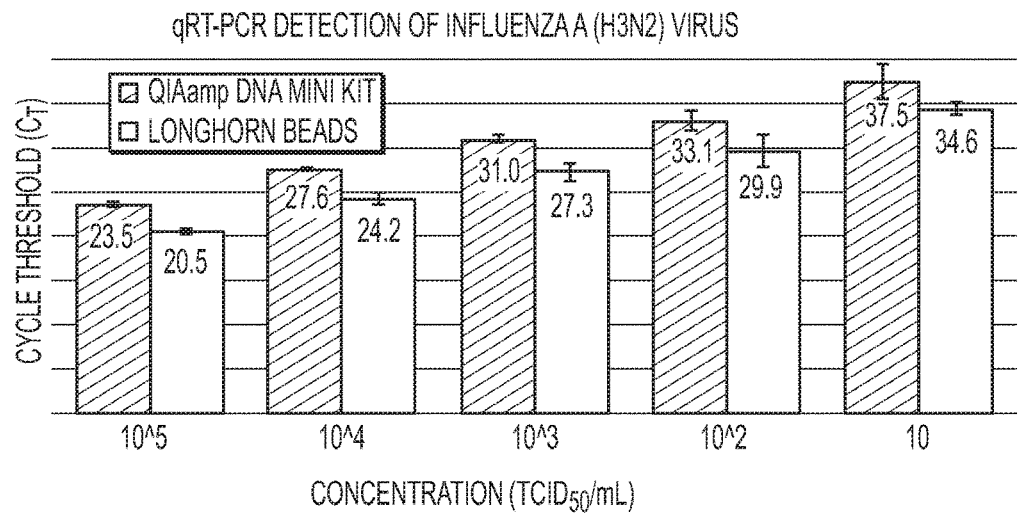
(FIG. 12A) influenza A virus.
Figure 12B:
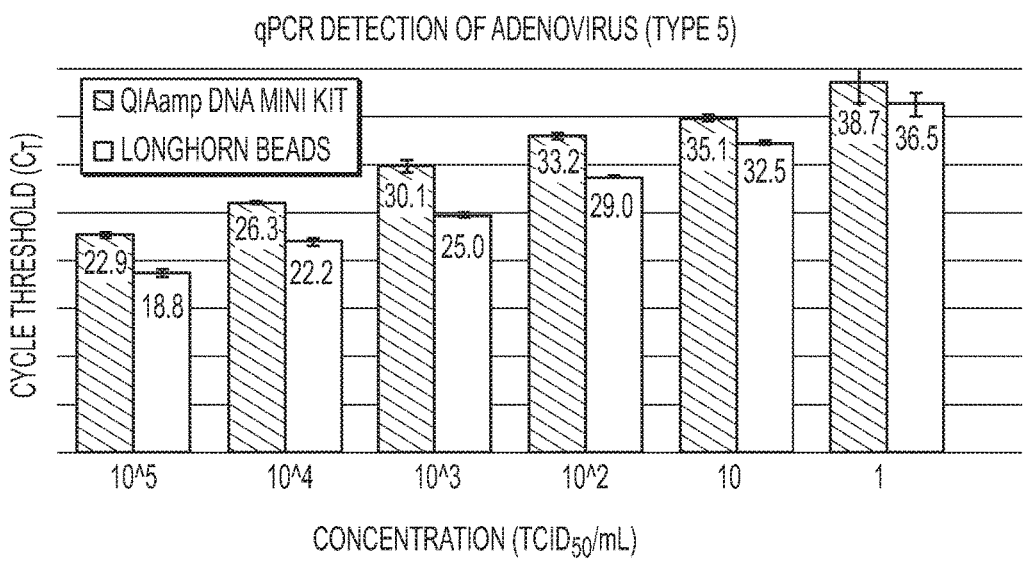
(FIG. 12B) adenovirus.
Figure 12C:
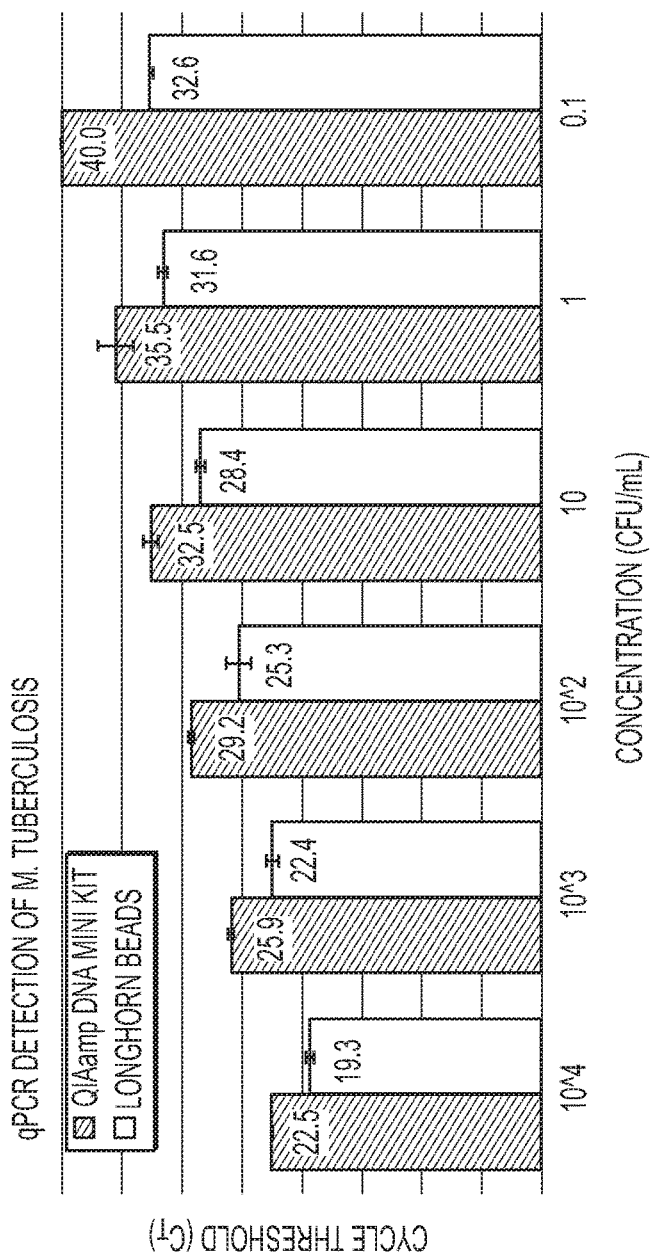
(FIG. 12C) *M. tuberculosis* from 10-fold dilutions in Primestore MTM. A $C_T$ value of 40 indicates not detected.
Figure 13A:
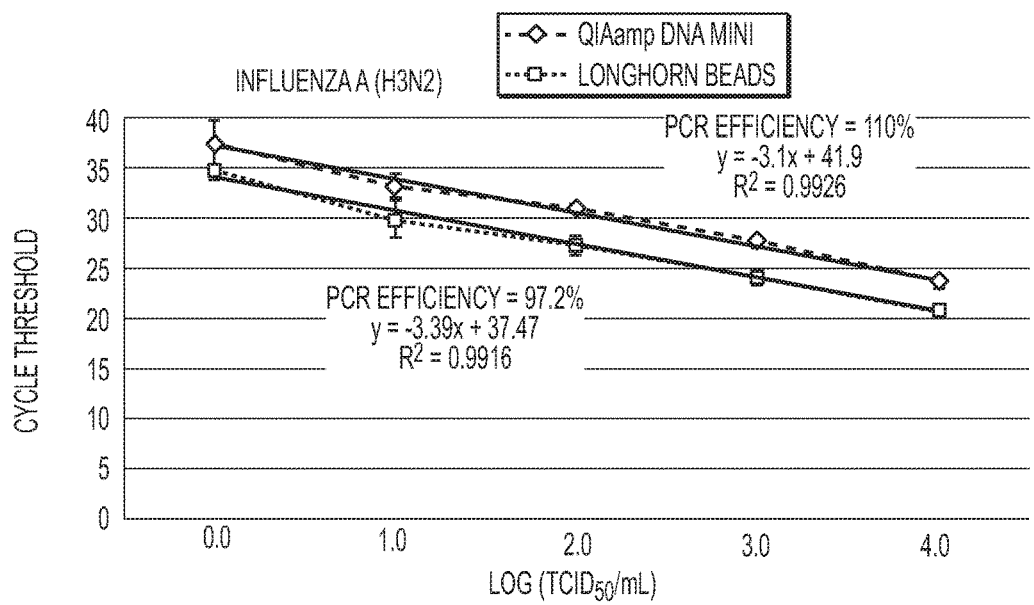
(FIG. 13A) influenza A virus.
Figure 13B:
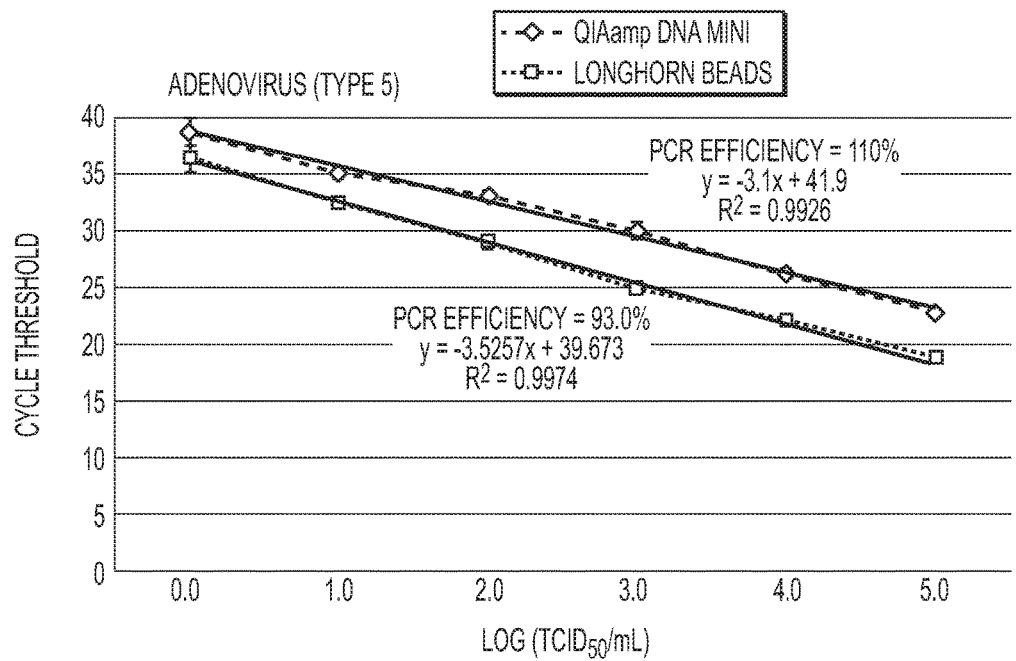
(FIG. 13B) adenovirus.
Figure 13C:
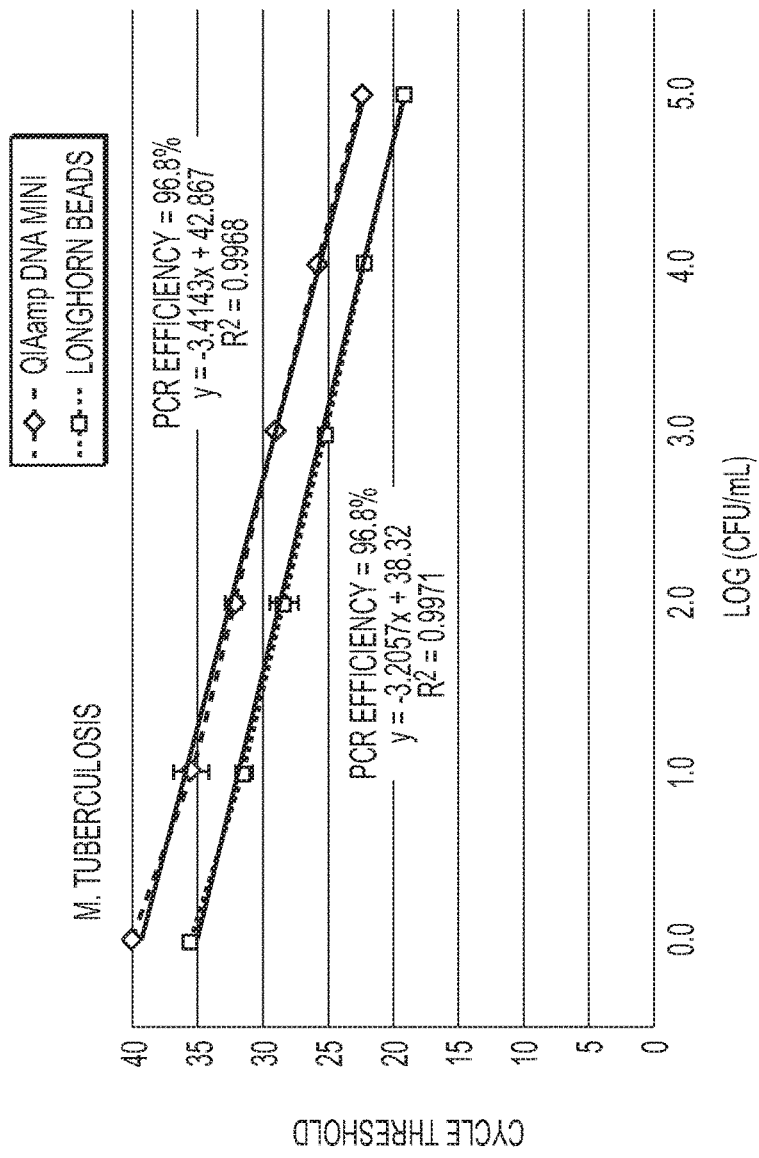
(FIG. 13C) *M. tuberculosis* in PS-MTM.

According to qPCR, bead-based extraction was more sensitive, i.e., lower cycle threshold ($C_T$) values at each dilution for influenza A (see FIG. 12A), Adenovirus (Type 5) (see FIG. 12B), and *Mycobacterium tuberculosis* (see FIG. 12C). At 1 CFU/ml, MTB was detected (avg. $C_T$=35.6; S.E.=1.4) using bead-based extraction, but not detected ($C_T$=40) from extraction using Qiagen. FIG. 13A indicates PCR efficiency with influenza A of 97.2% for bead-based vs. 110% for Qiagen. FIG. 13B indicates a PCR efficiency with Adenovirus (Type 5) of 93% for bead-based vs. 110% for Qiagen. FIG. 13C indicates a PCR efficiency with *M. tuberculosis* of 96.8 for bead-based vs. 96.8% for Qiagen. Each extraction was carried out in triplicate and plotted as the average of those determinations+/−the standard error. A $C_T$ value of 40 is not detected. Best-fit linear regression, slope and PCR efficiency are indicated. PCR efficiency E=(−1/slope)−1. To summarize, qPCR efficiencies were more improved using bead-based nucleic acid extraction (96.8%-97.2%) as compared to qPCR efficiencies obtained using Qiagen extraction (96.8%-110%). The bead-based approach offers a concentration factor to detect low level RNA/DNA. Magnetized beads and optimized chemistry produce cleaner extraction preparations yielding high purity. This methodology is also important for improving qPCR detection and next generation sequencing of pathogens directly from low target clinical specimens.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. U.S. Pat. No. 8,084,443 entitled "Biological Specimen Collection and Transport System and Method of Use," which issued Dec. 27, 2011; U.S. Pat. No. 8,080,645 entitled "Biological Specimen Collection/Transport Compositions and Methods," which issued Dec. 20, 2012, U.S. Pat. No. 8,097,419 entitled "Compositions and Method for Rapid, Real-Time Detection of Influenza A Virus (HIN1) Swine 2009," which issued Jan. 17, 2012, U.S. patent application Ser. No. 13/094,809 entitled "Compositions and Method for Detecting, Identifying and Quantitating Mycobacterial-Specific Nucleic Acid," which was filed Apr. 26, 2011, and International Application No. PCT/US2012/35253 entitled "Compositions and Method for Detecting and Identifying Nucleic Acids in Biological Samples," filed Apr. 26, 2012, are each specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method of extracting nucleic acids from a biological sample containing cells and/or microorganisms comprising:
adding a matrix material and a buffer to the biological sample, wherein the matrix material binds to nucleic acids of the sample;
isolating matrix material bound to nucleic acids of the sample;
adding an intermediate buffer that promotes a release of nucleic acids from the matrix material to form a mixture;
adding a chemically modified magnetic matrix material and a binding buffer to the mixture wherein the chemically modified matrix material comprises a ligand that binds to a specific nucleic acid sequence;
exposing the mixture to a magnetic field to concentrate the magnetic matrix material bound to the specific nucleic acid sequence; and
adding an extraction buffer to the concentrated magnetic matrix material wherein the specific nucleic acid sequence is extracted from the magnetic matrix material.

2. The method of claim 1, wherein the biological sample comprises human, animal, microbial or plant material.

3. The method of claim 1, wherein the matrix material comprises magnetic beads of silicone, porcelain, ceramic, plastic, glass or polymer.

4. The method of claim 1, wherein the matrix material disrupts the cells and/or microorganisms of the biological sample and binds to nucleic acids released from the disrupted cells and/or microorganisms.

5. The method of claim 1, wherein the matrix material does not disrupt the cells and/or microorganisms of the biological sample and binds to nucleic acids of the biological sample other than those present within the cells and/or microorganisms.

6. The method of claim 1, wherein the buffer comprises a chaotrope, a detergent, a reducing agent, a buffer and a chelator, together at a pH of between about 6-8.

7. The method of claim 1, wherein the buffer is a lysis buffer that lyses cells, inactivates nucleases, stabilizes macromolecules, and sterilizes the sample at ambient temperatures.

8. The method of claim 1, wherein the buffer is a non-cell lysis buffer that maintains the integrity of cells and/or microbes of the biological sample.

9. The method of claim 1, wherein the intermediate buffer causes the release of nucleic acids from the matrix material and has a pH above 7.

10. The method of claim 1, wherein the intermediate buffer comprises TE, saline, an alkaline solution, NALC or a combination thereof.

11. The method of claim 1, wherein the chemical modification of the chemically modified magnetic matrix material is a carboxy group.

12. The method of claim 1, wherein the specific nucleic acid comprises a cancer marker, a sequence indicating the presence of a pathogenic organism or infection, a sequence that is characteristic of a phenotypic condition, a sequence indicating a lineage, a sequence indicating an identifiable characteristic, a sequence indicating a mutation, a sequence indicating a change from a wild-type sequence, or a combination thereof.

13. The method of claim 1, wherein the specific nucleic acid sequence is indicative of the presence of a pathogen.

14. The method of claim 13, wherein the pathogen is a virus, a bacterium, a parasite or a fungus.

15. The method of claim 1, wherein the binding buffer comprises PEG, a salt, a buffering agent, a chelator, a detergent, and an alcohol.

16. The method of claim 1, wherein the magnetic field is an electro-magnetic field.

17. The method of claim 1, wherein the extraction buffer comprise water, TE, saline, alcohol or a combination thereof.

18. The method of claim 1, wherein the extracted nucleic acids are identifiable by molecular analysis.

19. The method of claim 18, wherein the molecular analysis comprises a PCR.

20. The method of claim 1, which does not involve centrifugation or nucleic acid purification.

21. The method of claim 1, which is automated for high-throughput analysis of a plurality of biological samples.

22. The method of claim 1, wherein extraction efficiency, as measured by PCR cycle threshold, is lower as compared with extraction efficiency for a conventional extraction procedure.

23. The method of claim 22, wherein the conventional extraction procedure is a silica spin column extraction.

24. A method of extracting nucleic acids from a biological sample containing cells and/or microorganisms comprising:
combining the biological sample with magnetic silicon dioxide beads and a lysis buffer to form a solution, wherein the beads bind to nucleic acids of the sample;
exposing the solution to a magnetic field and removing liquid to concentrate the beads;
adding an alkaline buffer to the concentrated magnetic beads to form a mixture, wherein the alkaline buffer causes the release of nucleic acids from the silicon dioxide beads;
adding carboxy-modified magnetic beads in a binding buffer to the mixture wherein the carboxy-modified magnetic beads bind to a predetermined nucleic acid sequence;
exposing the mixture to a magnetic field and removing liquid to isolate the carboxy-modified magnetic beads bound to the predetermined nucleic acid sequence; and
eluting the predetermined nucleic acid sequences from the carboxy-modified magnetic beads using purified water and/or a Tris-EDTA buffer.

25. The method of claim 24, wherein the lysis buffer comprises a chaotrope, a detergent, a reducing agent, a buffer, and a chelator at a pH of about 6-8.

26. The method of claim 24, wherein the binding buffer comprises PEG, a salt, a buffering agent, a chelator, a detergent, NLS and an alcohol.

27. The method of claim 24, which does not involve centrifugation.

28. The method of claim 24, which is automated for high-throughput analysis of a plurality of biological samples.

29. The method of claim 24, wherein extraction efficiency, as measured by PCR cycle threshold, is lower as compared with extraction efficiency for a conventional extraction procedure.

30. The method of claim 29, wherein the conventional extraction procedure is a silica spin column extraction.

31. The method of claim 24, further comprising analyzing the isolated nucleic acids by a PCR.

32. A kit comprising:
a solution that comprises a matrix material and a buffer;
an intermediate buffer with a pH above 7; and
carboxy-modified magnetic beads in a binding buffer, wherein the carboxy-modified magnetic beads bind to a specific nucleic acid sequence.

33. The kit of claim 32, wherein the buffer comprises a chaotrope, a detergent, a reducing agent, a buffer and a chelator at a pH of about 6-8.

34. The kit of claim 33, wherein the buffer lyses cells, inactivates nucleases, stabilizes nucleic acids, and sterilizes the sample at ambient temperatures.

35. The kit of claim 32, wherein the buffer is a non-lysis buffer that maintains the integrity of cells and/or microbes.

36. The kit of claim 32, wherein the matrix material comprises silica dioxide beads.

37. The kit of claim 32, wherein the intermediate buffer has a pH of 8 or more.

38. The kit of claim 32, wherein the intermediate buffer has a pH of 9 or more.

39. The it of claim 32, wherein the binding buffer comprises a combination of PEG, a salt, a chelator, a detergent, NLS and an alcohol.

40. The kit of claim 32, further comprising a magnet or electromagnet.

41. The method of claim 1, which is performed in a single vessel.

42. The method of claim 24, which is performed in a single vessel.

* * * * *